(12) United States Patent
Palo

(10) Patent No.: US 6,376,843 B1
(45) Date of Patent: Apr. 23, 2002

(54) METHOD OF CHARACTERIZING FLUORESCENT MOLECULES OR OTHER PARTICLES USING GENERATING FUNCTIONS

(75) Inventor: Kaupo Palo, Haabneeme (EE)

(73) Assignee: Evotec OAI AG, Hamburg (DE)

( * ) Notice: Subject to any disclaimer, the term of this patent is extended or adjusted under 35 U.S.C. 154(b) by 0 days.

(21) Appl. No.: 09/338,439

(22) Filed: Jun. 23, 1999

(51) Int. Cl.⁷ .............................................. G01N 21/64
(52) U.S. Cl. .............................. 250/458.1; 250/459.1
(58) Field of Search ........................... 250/458.1, 459.1, 250/461.1, 461.2

(56) References Cited

FOREIGN PATENT DOCUMENTS

| DE | 29913707 U1 * | 12/1999 | ........... G02B/21/00 |
|----|---------------|---------|------------------------|
| EP | 0836090 A1 | 4/1998 | |
| WO | WO 98/16814 | 4/1998 | |
| WO | 98/23941 | 6/1998 | |

OTHER PUBLICATIONS

Hong Qian et al., "Distribution of Molecular Aggregation by Analysis of Fluctuation Moments", vol. 87, pp. 5479–5483, Jul. 1990.

Qian et al., "On the analysis of high order moments of fluorescence fluctuations," *Biophysical Journal*, 57:375–380 (Feb. 1990).

* cited by examiner

Primary Examiner—Constantine Hannaher
(74) Attorney, Agent, or Firm—Jacobson Holman, PLLC

(57) ABSTRACT

A method characterizes fluorescent molecules or other particles in samples by a) monitoring fluctuating intensity of fluorescence emitted by the molecules or other particles in at least one measurement volume of a non-uniform spatial brightness profile by measuring numbers of photon counts in primary time intervals by a single or more photon detectors, b) determining at least one distribution function of numbers of photon counts, $\hat{P}(n)$, from the measured numbers of photon counts, c) determining physical quantities characteristic to the particles by fitting the experimentally determined distribution function of numbers of photon counts, wherein the fitting procedure involves calculation of a theoretical distribution function of the number of photon counts $P(n)$ through its generating function, defined as $$G(\zeta) = \sum_n \zeta^n P(n).$$

17 Claims, 23 Drawing Sheets

(6 of 23 Drawing Sheet(s) Filed in Color)

| Cleavage | ●—▭—● | ●—▭ | ▭—● |
|---|---|---|---|
| | | Intensity / kHz | |
| none | $Q_{01}$ = 43/109 (48/52)* | $Q_{02}$ = 16/60 (9/91)* | $Q_{03}$ = 25/66 (12/88)* |
| Hind III | $Q_1$ = 60<br>$Q_2$ = 22 | $Q_1$ = 58 | $Q_2$ = 26 |
| Kpn I | $Q_3$ = 15<br>$Q_4$ = 66 | $Q_3$ = 12 | $Q_4$ = 60 |
| Hind III/Kpn I | $Q_2$ = 24<br>$Q_3$ = 10 | $Q_3$ = 12 | $Q_2$ = 28 |

Concentration ratio (%) of two signals. See text for details.

METHOD OF CHARACTERIZING FLUORESCENT MOLECULES OR OTHER PARTICLES USING GENERATING FUNCTIONS

This invention relates to the field of fluorescence spectroscopy, and more particularly to a method for determining characteristic physical quantities of fluorescent molecules or other particles present in a sample.

The primary data of an experiment in fluorescence correlation spectroscopy (FCS) is a sequence of photon counts detected from a microscopic measurement volume. An essential attribute of the fluorescence correlation analysis is the calculation of the second order autocorrelation function of photon detection. This is a way how a stochastic function (of photon counts) is transformed into a statistical function having an expected shape, serving as a means to estimate some parameters of the sample. However, the calculation of the autocorrelation function is not the only way for extracting information about the sample from the sequence of photon counts. Further approaches are based on moment analysis and analysis of the distribution of the number of photon counts per given time interval (Qian and Elson, Proc. Natl. Acad. Sci. USA, 87:5479–483, 1990; Qian and Elson, Biophys. J. 57:375–380, 1990).

The intensity of fluorescence detected from a particle within a sample is not uniform but depends on the coordinates of the particle with respect to the focus of the optical system. Therefore, a reliable interpretation of measurements should account for the geometry of the illuminated measurement volume. Even though the calculation of a theoretical distribution of the number of photo counts is more complex for a bell-shaped profile than for a rectangular one, the distribution of the number of photon counts sensitively depends on values of the concentration and the specific brightness of fluorescent species, and therefore, the measured distributions of the number of photon counts can be used for sample analysis. The term "specific brightness" denotes the mean count rate of the detector from light emitted by a particle of given species situated in a certain point in the sample, conventionally in the point where the value of the spatial brightness profile function is unity.

The first realization of this kind of analysis was demonstrated on the basis of moments of the photon count number distribution (Qian and Elson, Proc. Natl. Acad. Sci. USA, 87: 5479–483, 1990). The k-th factorial moment of the photon count number distribution P(n) is defined as $$F_k = \sum_n \frac{n!}{(n-k)!} P(n). \tag{1}$$

In turn, factorial moments are closely related to factorial cumulants, $$F_k = \sum_{l=0}^{k-1} C_l^{k-1} K_{k-l} F_l, \tag{2}$$

or $$K_l = F_k - \sum_{i=1}^{k-1} C_l^{k-1} K_{k-l} F_i. \tag{3}$$

($C_l^k$s are binomial coefficients, and $K_k$s are cumulants). The basic expression used in moment analysis, derived for ideal solutions, relate k-th order cumulant to concentrations ($c_l$) and specific brightness values ($q_l$).

$$K_k = \chi_k \sum_i c_i (q_i T)^k. \tag{4}$$

Here, $X_k$ is the k-th moment of the relative spatial brightness profile B(r):

$$\chi_k = \int_{(V)} B^k(r) dV. \tag{5}$$

Usually in FCS, the unit of volume and the unit of B are selected which yield $X_1 = X_2 = 1$. After selecting this convention, concentrations in the equations are dimensionless, expressing the mean number of particles per measurement volume, and the specific brightness of any species equals the mean count rate from a particle if situated in the focus divided by the numeric value of B(0). The value of this constant is characteristic of optical equipment. It can be calculated from estimated parameters of the spatial intensity profile (see below). Qian and Elson used experimental values of the first three cumulants to determine unknown parameters of the sample. The number of cumulants which can be reliably determined from experiments is usually three to four. This sets a limit to the applicability of the moment analysis.

The idea behind the so-called fluorescence intensity distribution analysis (FIDA), which has in detail been described in the international patent application PCT/EP 97/05619 (international publication number WO 98/16814), can be well understood by imagining an ideal case when a measurement volume is uniformly illuminated and when there is almost never more than a single particle illuminated at a time, similar to the ideal situation in cell sorters. Under these circumstances, each time when a particle enters the measurement volume, fluorescence intensity jumps to a value corresponding to the brightness of a given type of particles. Naturally, the probability that this intensity occurs at an arbitrary time moment equals the product of the concentration of a given species and the size of the measurement volume. Another fluorescent species which may be present in the sample solution produces intensity jumps to another value characteristic of this other species. In summary, the distribution of light intensity is in a straight-forward way determined by the values of concentration and specific brightness of each fluorescent species in the sample solution.

It is assumed that the light intensity reaching the detector from a particle as a function of coordinates of the particle is constant over the whole measurement volume, and zero outside it. Also, it is assumed that the diffusion of a fluorescent particle is negligible during the counting interval T. In this case, the distribution of the number of photon counts emitted by a single fluorescent species can be analytically expressed as double Poissonian: the distribution of the number of particles of given species within this volume is Poissonian, and the conditional probability of the number of detected photons corresponding to a given number of particles is also Poissonian. The double Poissonian distribution has two parameters: the mean number of particles in the measurement volume, c and the mean number of photons emitted by a single particle per dwell time, qT. The distribution of the number of photon counts n corresponding to a single species is expressed as $$P(n; c, q) = \sum_{n=0}^{\infty} \frac{c^m}{m!} e^{-c} \frac{(mqT)^n}{n!} e^{-mqT}, \qquad (6)$$

where m runs over the number of molecules in the measurement volume. If $P_i(n)$ denotes the distribution of the number of photon counts from species i, then the resultant distribution $P(n)$ is expressed as $$P(n) = \sum_{\{n_l\}} \prod_l P_l(n_l) \delta\left(n, \sum_i n_i\right) \qquad (7)$$

This means that $P(n)$ can be calculated as a convolution of the series of distribution $P_i(n)$.

Like in FCS, the rectangular sample profile is a theoretical model which can hardly be applied in experiments. One may divide the measurement volume into a great number of volume elements and assume that within each of them, the intensity of a molecule is constant. Contribution to photon count number distribution from a volume element is therefore double Poissonian with parameters cdV and qTB(r). (Here q denotes count rate from a molecule in a selected standard position where B=1, and B(r) is the spatial brightness profile function of coordinates). The overall distribution of the number of photon counts can be expressed as a convolution integral over double Poissonian distributions. Integration is a one-dimensional rather than a three-dimensional problem here, because the result of integration does not depend on actual positions of volume elements in response to each other. Figuratively, one may rearrange the three-dimensional array of volume elements into a one-dimensional array, for example in the decreasing order of the value of B.

In a number of first experiments described in the international patent application PCT/EP 97/05619, the photon count number distribution was indeed fitted, using the convolution technique. The sample model consisted of twenty spatial sections, each characterized by its volume $V_j$ and brightness $B_j$. However, the technique described in this patent application is slow and inconvenient in cases involving a high number of samples to be analyzed, like in diagnostics or drug discovery, or in analyzing distribution functions involving more than a single argument.

Therefore, it is an object of the present invention to present a convenient and much faster technique for analyzing fluorescence intensity fluctuations.

According to the present invention there is provided a method for characterizing fluorescent molecules or other particles in samples, the method comprising the steps of:
  a) monitoring fluctuating intensity of fluorescence emitted by the molecules or other particles in at least one measurement volume of a non-uniform spatial brightness profile by measuring numbers of photon counts in primary time intervals by a single or more photon detectors,
  b) determining at least one distribution function of numbers of photon counts, $\hat{P}(n)$, from the measured numbers of photon counts,
  c) determining physical quantities characteristic to said particles by fitting the experimentally determined distribution function of numbers of photon counts, wherein the fitting procedure involves calculation of a theoretical distribution function of the number of photon counts $P(n)$ through its generating function, defined as $$G(\xi) = \sum_n \xi^n P(n).$$

The formal definition of the generating function of a distribution $P(n)$ is as follows:

$$G(\xi) = \sum_{n=0}^{\infty} \xi^n P(n). \qquad (8)$$

What makes the generating function attractive in count number distribution analysis is the additivity of its logarithm: logarithms of generating functions of photon count number distributions of independent sources, like different volume elements as well as different species, are simply added for the calculation of the generating function of the combined distribution because the transformation (8) maps distribution convolutions into the products of the corresponding generating functions.

In a particular preferred embodiment, one might monitor the fluctuating fluorescence intensity in consecutive primary time intervals of equal width. Typical primary time intervals have a width in order of several tenth of microseconds. The total data collection time is usually several tenth of seconds.

In a further preferred embodiment, numbers of photon counts $\{n_i\}$ subject to determination of a distribution function $\hat{P}(n)$ in step b) are derived from numbers of photon counts in primary time intervals $\{N_j\}$ by addition of numbers of photon counts from primary time intervals according to a predetermined rule. One might e.g. be interested in choosing numbers of photon counts $\{n_i\}$ subject to determination of a distribution function $\hat{P}(n)$ which are calculated from the numbers of photon counts in primary time intervals $\{N_j\}$ according to the rule $$n_i = \sum_{k=1}^{M} N_{Mi+k},$$

where M is an integer number expressing how many times the time interval in which $\{n_i\}$ is determined is longer than the primary time interval.

In a further embodiment, numbers of photon counts $\{n_i\}$ are derived from predetermined primary time intervals according to a rule in which primary time intervals are separated by a time delay. In particular, the following rule can be applied:

$$n_i = \sum_{k=1}^{M} (N_{Mi+k} + N_{M(i+L)+k}),$$

where M and L are positive integer numbers, $\{n_i\}$ are numbers of photon counts subject to determination of a distribution function $\hat{P}(n)$, and $\{N_j\}$ are the numbers of photon counts in primary time intervals.

In some cases, it might be preferred to determine not only a single distribution function in step b), but rather a set of distribution functions $\hat{P}(n)$. These can be determined according to a set of different rules, said set of distribution functions being fitted jointly in step c). As an example a set of distribution functions with different values of M and/or L might be fitted jointly.

Typical physical quantities which might be determined in step c) according to the present invention are concentration, specific brightness and/or diffusion coefficient of molecules or other particles.

In a further preferred embodiment, the generating function is calculated using the expression $$G(\xi) = \exp[\int dq c(q) \int d^3 r(e^{(\xi-1)qTB(r)} - 1)],$$

where c(q) is the density of particles with specific brightness q, T is the length of the counting interval, and B(r) is the spatial brightness profile as a function of coordinates.

Applying the definition (8) to formula (6) with $c \to cdV$ and $q \to qB(r)$, the contribution from a particular species and a selected volume element dV can be written as $$G_i(\xi; dV) = \exp[c_i dV(c_i dV(e^{(\xi-1)q_i TB(r)} - 1)]. \tag{9}$$

Therefore, the generating function of the total photon count number distribution can be expressed in a closed form $$G(\xi) = \exp\left[\sum_i c_i \int (e^{(\xi-1)q_i TB(r)} - 1) dV\right]. \tag{10}$$

Numeric integration according to Eq. (9) followed by a fast Fourier transform is the most effective means of calculating the theoretical distribution P(n) corresponding to a given sample (i.e., given concentrations and specific brightness values of fluorescent species). If one selects $\xi = e^{1p}$, then the distribution P(n) and its generating function $G(\phi)$ are interrelated by the Fourier transform. Therefore, it is particularly preferred to select the argument of the generating function in the form $\xi = e^{-1p}$ and to use a fast Fourier transform algorithm in calculation of the theoretical distribution of the number of photon counts out of its generating function.

When calculating the theoretical distribution P(n) in step c) according to the present invention, the spatial brightness profile might be modeled by a mathematical relationship between volume and spatial brightness. In particular, one might model the spatial brightness profile by the following expression:

$$\frac{dV}{dx} = a_1 x + a_2 x^2 + a_3 x^3,$$

where dV denotes a volume element, x denotes logarithm of the relative spatial brightness, and $\alpha_1$, $\alpha_2$ and $\alpha_3$ are empirically estimated parameters.

Some fluorescent species may have a significantly wide distribution of specific brightness. For example vesicles, which are likely to have a significantly broad size distribution and a random number of receptors, may have trapped a random number of labeled ligand molecules. In order to fit count number distributions for samples containing such kind of species, it is useful to modify Eq. (10) in the following manner. The assumption is made that the distribution of brightness of particles q within a species is mathematically expressed as follows:

$$p(q) \; q^{a-1} e^{-bq}. \tag{11}$$

This expression has been selected for the sake of convenience: all moments of this distribution can be analytically calculated, using the following formula:

$$\int_0^\infty x^a e^{-bx} dx = \frac{\Gamma(a+1)}{b^{a+1}}. \tag{12}$$

It is straightforward to derive the modified generating function of a photon count number distribution. One can rewrite Eq. (9) as follows:

$$G(\xi) = \exp\left[\sum_i c_i \int dV \int_0^\infty dq \rho(q; a_i, b_i)(e^{(\xi-1)qTB(r)} - 1)\right], \tag{13}$$

where $$\rho(q; a, b) = \frac{b^a}{\Gamma(a)} q^{n-1} e^{-bq}. \tag{14}$$

The integral over q can be performed analytically:

$$G(\xi) = \exp\left\{\sum_i c_i \int dV \left[\left(\frac{b_i}{b_i - (\xi-1)TB(x)}\right)^{a_1} - 1\right]\right\}. \tag{15}$$

The parameters $\alpha_i$ and $b_i$ are related to the mean brightness $\bar{q}_i$ and the width of the brightness distribution $\sigma_i^2$ by $$a_i = \frac{\bar{q}_i^2}{\sigma_i^2}, \quad b_i = \frac{\bar{q}_i}{\sigma_i^2}. \tag{16}$$

In the range of obtained count numbers, the probability to obtain a particular count number usually varies by many orders of magnitude, see for example the distribution of FIG. 1. Consequently, the variance of the number of events with a given count number has a strong dependence on the count number. To determine weights for least squares fitting, one may assume that light intensities in all counting intervals are independent. Under this assumption, one has a problem of distributing M events over choices of different count numbers n, each particular outcome having a given probability of realization, P(n). Covariance matrix elements of the distribution can be expressed as follows:

$$\langle \Delta P(n) \Delta P(m) \rangle = \frac{P(n) \delta(n, m) - P(n) P(m)}{M}, \tag{17}$$

where M is the number of counting intervals per experiment.

For a further simplification, one may ignore the second term on the right side of Eq. (17), which can be interpreted as a consequence of normalization. In this case, the weights simply equal to the inverse values of the diagonal covariance matrix elements $$W_n = \frac{M}{P(n)}. \tag{18}$$

Dispersion matrix (17) corresponds to the multinomial distribution of statistical realizations of histograms. The Poissonian distribution, with the constraint that the total number of counting intervals M is fixed, will lead to the multinomial distribution. This is the rationale behind using Poissonian weights as given in Eq. (18).

Let $n_k$ be the expectation value of the number of events of counting k photons and let $$N = \sum_k n_k$$

be their sum. Let $m_k$ be a statistical realization with $$M = \sum_k m_k.$$

Assume that realizations $m_0, m_1, \ldots$ obey Poissonian statistics $$P(m_0, m_1, \ldots) = \frac{[n_0, n_1, \ldots]^{[m_0, m_1, \ldots]}}{[m_0, m_1, \ldots]!} e^{-N}, \quad (19)$$

where we have introduced the notation $$n_0^{m_0} n_1^{m_1} \ldots \equiv [n_0, n_1, \ldots]^{[m_0, m_1, \ldots]}$$

and $$m_0! m_1! \ldots \equiv [m_0, m_1, \ldots]!.$$

The probability of having the total of M events is $$P(M) = \frac{N^M}{N!} e^{-N}. \quad (20)$$

The conditional probability of having $m_0, m_1, \ldots$ events if there is a total of M events is $$P(m_0, m_1, \ldots | M) \equiv \frac{P(m_0, m_1, \ldots)}{P(M)} = \frac{M! [n_0, n_1, \ldots]^{[m_0, m_1, \ldots]}}{N^M [m_0, m_1, \ldots]!},$$

or $$P(m_0, m_1, \ldots | M) \equiv C_{m_0, m_1, \ldots}{}^M [p_0, p_1, \ldots]^{[m_0, m_1, \ldots]}, \quad (21)$$

This is the multinomial distribution where we have introduced:

$$p_k \equiv \frac{n_k}{M}$$

and $C_{m_0, m_1, \ldots}{}^M$ are multinomial coefficients.

In general, a linear or linearized least squares fitting returns not only the values of the estimated parameters, but also their covariance matrix, provided the weights have been meaningfully set. It may turn out to be possible to express the statistical errors of the estimated parameters analytically in some simple cases (e.g., for the rectangular sample profile and single species) but in applications at least two-component analysis is usually of interest. Therefore, one may be satisfied with the numerical calculations of statistical errors. In addition to the „theoretical" errors with the assumption of non-correlated measurements (Eq. (17)), in some cases statistical errors have been estimated empirically, making a series of about a hundred FIDA experiments on identical conditions. As a rule, empirical errors are higher than theoretical ones by a factor of three to four. Empirical errors appear to be closer to the theoretical ones in scanning experiments. Therefore we are convinced that the main reason of the underestimation of theoretical errors is the assumption of non-correlated measurements. Table 1 compares statistical errors of parameters estimated by fitting a photon count number distribution (FIDA) according to the present invention and by the moment analysis. Error values are determined through processing a series of simulated distributions. The present invention is overwhelmingly better than the moment analysis if the number of estimated parameters is higher than three.

TABLE 1

| Data collection time, s | Primary time interval, μs | Number of species | Number of estimated parameters | Parameter specification | Value (qs in kHz) | Percent error of FIDA (invention) | Percent error of moment analysis |
|---|---|---|---|---|---|---|---|
| 10.0 | 40.0 | 1 | 2 | c | 0.5 | 0.59 | 0.54 |
|  |  |  |  | q | 60.0 | 0.56 | 0.51 |
| 10.0 | 40.0 | 2 | 3 | $c_1$ | 0.05 | 2.00 | 2.71 |
|  |  |  |  | $q_1$ | 150.0 | 1.54 | 1.89 |
|  |  |  |  | $c_2$ | 3.0 | 0.53 | 0.62 |
|  |  |  |  | $q_2$ | 5.0 (fixed) |  |  |
| 10.0 | 40.0 | 2 | 4 | $c_1$ | 0.05 | 2.26 | 4.99 |
|  |  |  |  | $q_1$ | 150.0 | 1.63 | 2.53 |
|  |  |  |  | $c_2$ | 3.0 | 3.18 | 17.8 |
|  |  |  |  | $q_2$ | 5.0 | 3.35 | 14.9 |

Confocal techniques may be applied to a wide field of applications, such as biomedicine, diagnostics, high through-put drug screening, sorting processes such as sorting of particles like beads, vesicles, cells, bacteria, viruses, etc. The conjugate focal (confocal) technique is based on using a point source of light sharply focused to a diffraction-limited spot on the sample. The emitted light is viewed through a spatial filter (pinhole) that isolates the viewing area to that exactly coincident with the illuminating spot. Thus, the illumination and detection apertures are optically conjugated with each other. Light originating from focal planes other than that of the objective lens is rejected, which effectively provides a very small depth of field. Therefore, in a particular preferred embodiment of the present invention, in step a) a confocal microscope is used for monitoring the intensity of fluorescence. In order to achieve a high signal-to-noise ratio, it is useful to monitor the intensity of fluorescence using an apparatus that comprises: a radiation source (12) for providing excitation radiation (14), an objective (22) for focussing the excitation radiation (14) into a measurement volume (26), a detector (42) for detecting emission radiation (30) that stems from the measurement volume (26), and an opaque means (44) positioned in he pathway (32) of the emission radiation (30) or excitation radiation (14) for erasing the central part of the emission radiation (30) or excitation radiation (14). It might be particularly preferred to use an optical set-up described in detail in FIG. 9.

In a further preferred embodiment, the method according to the present invention is applied to fit a joint distribution of photon count numbers. In experiments, fluorescence from a microscopic volume with a fluctuating number of molecules is monitored using an optical set-up (e.g. a confocal microscope) with two detectors. The two detectors may have different polarizational or spectral response. In one embodiment, concentrations of fluorescent species together with two specific brightness values per each species are determined. The two-dimensional fluorescence intensity distribution analysis (2D-FIDA) if used with a polarization cube is a tool which can distinguish fluorescent species with different specific polarization ratios. This is a typical example of a joint analysis of two physical characteristics of single molecules or other particles, granting a significantly improved reliability compared to methods focussed on a single physical characteristic.

In order to express the expected two-dimensional distribution of the number of photon counts, it is favourable to use the following assumptions: (A) Coordinates of particles are random and independent of each other. (B) Contribution to fluorescence intensity from a particle can be expressed as a product of a specific brightness of the particle and a spatial brightness profile function characteristic to the optical equipment. (C) A short counting time interval T is selected, during which brightness of fluorescent particles does not significantly change due to diffusion.

At first, a joint distribution of count numbers from a single fluorescent species and a single small open volume element dV is expressed. The volume element is characterized by coordinates r and spatial brightness B(r), and the fluorescent species is characterized by its specific brightness values $q_1$ and $q_2$. By $q_1$ and $q_2$, mean photon count rates by two detectors from a particle situated at a point where B(r)=1 are denoted. A convenient choice is to select a unit of B, as usual in FCS, by the equation $X_1=X_2$, where $X_1=\int B^k(r)d^3r$. If the volume element happens to contain m particles, then the expected photon count numbers per time interval T from the volume element are $mq_1TB(r)$ and $mq_2TB(r)$, while the distribution of numbers of photon counts from m particles $P(n_1,n_2|m)$ is Poissonian for both detectors independently:

$$P(n_1, n_2 \mid m) = \frac{(mq_1 TB(x))^{n_1}}{n_1!} e^{-mq_1 TB(x)} \frac{(mq_2 TB(x))^{n_2}}{n_2!} e^{-mq_2 TB(x)}. \quad (22)$$

From the other side, under assumption (A), the distribution of the number of particles of given species in the volume element is Poissonian with mean cdV, c denoting concentration:

$$P_{dV}(m) = \frac{(cdV)^m}{m!} e^{-cdV}. \quad (23)$$

The overall distribution of the number of photon counts from the volume element can be expressed using Eqs.22 and 23:

$$P_{dV}(n_1, n_2) = \sum_m P_{dV}(m) P(n_1, n_2 \mid m) \quad (24)$$

$$= \sum_m \frac{(cdV)^m}{m!} e^{-cdV} \frac{(mq_1 TB(r))^{n_1}}{n_1!} e^{-mq_1 TB(r)} \frac{(mq_2 TB(r))^{n_2}}{n_2!} e^{-mq_2 TB(r)}$$

As in the one-dimensional case described above, a useful representation of a distribution of numbers of photon counts $P(n_1,n_2)$ in its generating function, defined as $$G(\xi_1, \xi_2) = \sum_{n_1=0}^{\infty} \sum_{n_2=0}^{\infty} \xi_1^{n_1} \xi_2^{n_2} P(n_1, n_2). \quad (25)$$

The generating function of the distribution expressed by Eq 24 can be written as $$G_{dV}(\xi_1, \xi_2) = e^{-cdV} \sum_m \frac{(cdV)^m}{m!} e^{-mq_1 BT} e^{-mq_2 BT} \sum_{n_1} \frac{(m\xi_1 qBT)^{n_1}}{n_1!} \quad (26)$$

$$\sum_{n_2} \frac{(m\xi_2 qBT)^{n_2}}{n_2!}$$

$$= e^{-cdV} \sum_m \frac{\{cdV \exp[(\xi_1 - 1)q_1 BT] \exp[(\xi_2 - 1)q_2 BT]\}^m}{m!}$$

$$= \exp[cdV(e^{(\xi_1-1)q_1 BT} e^{(\xi_2-1)q_2 BT} - 1)]$$

In particular, if one selects $\xi_k = \exp(i\phi_k)$, then the distribution $P(n_1,n_2)$ and its generating function $G(\phi_1,\phi_2)$ are interrelated by a 2-dimensional Fourier transform. What makes the generating function attractive in photon count number distribution analysis is the additivity of its logarithm: logarithms of generating functions of photon count number distributions of independent sources, like different volume elements as well as different species, are simply added for the calculation of the combined distribution. Therefore, the generating function of the overall distribution of the number of photon counts can be expressed in a closed form:

$$G(\xi_1, \xi_2) = \exp\left[(\xi_1 - 1)\lambda_1 T + (\xi_2 - 1)\lambda_2 T + \sum_i c_i \int (e^{(\xi_1-1)q_1 TB(r)(\xi_2-1)q_2 TB(r)} - 1) d^3 r \right]. \quad (27)$$

In this formula, a contribution from background count rates, $\lambda_1$ by detector 1 and $\lambda_2$ by detector 2, as well as contributions from different fluorescent species, denoted by the subscript i, have been integrated. Numeric integration according to Eq 27 followed by a fast Fourier transform is a very efficient means for calculation of the theoretical distribution $P(n_1,n_2)$ corresponding to a given sample (i.e. given concentrations and specific brightness values of fluorescent species).

The spatial brightness function is accounted through the spatial integration on the right side of Eq. 27. The three-dimensional integration can be reduced to a one-dimensional one by replacing three-dimensional coordinates r by a one-dimensional variable, a monotonic function of the spatial brightness B(r). A convenient choice of the variable is $x=\ln[B(0)/B(r)]$. A sufficiently flexible model of the spatial brightness profile is presented by the following expression:

$$\frac{dV}{dx} \propto x(1 + a_1 x + a_2 x^2). \tag{28}$$

In the interval of obtained count numbers, the probability to obtain a particular pair of count numbers usually varies by many orders of magnitude. Consequently, the variance of the experimental distribution has also a strong dependence on the count numbers. To determine weights for least squares fitting, for simplification it is assumed that coordinates of particles in all counting intervals are randomly selected. (This means one ignores correlations of the coordinates in consecutive counting intervals.) Under this assumption, one has a problem of distributing M events over choices of different pairs of count numbers $n_1$, $n_2$, each particular outcome having a given probability of realization, $P(n_1,n_2)$. Covariance matrix elements of the distribution can be expressed as follows:

$$\langle \Delta P(n_1, n_2) \Delta P(n'_1, n'_2) \rangle = \tag{29}$$

$$\frac{P(n_1, n_2)\delta(n_1, n'_1)\delta(n_2, n'_2) - P(n_1, n_2)P(n'_1, n'_2)}{M}.$$

where M is the number of counting intervals per experiment.

For a further simplification, one may ignore the second term on the right side of Eq. (29), which can be interpreted as a consequence of normalization. In this case, the weights simply equal to the inverse values of the diagonal covariance matrix elements $$W(n_1, n_2) = \frac{M}{P(n_1, n_2)}. \tag{30}$$

In general, a linearized least squares fitting algorithm returns not only values of estimated parameters, but also their covariance matrix, provided weights have been meaningfully set. In addition to "theoretical" errors corresponding to the assumption of uncorrelated measurements (Eq. (30)), in some cases statistical errors have been determined empirically, making a series of about 100 2D-FIDA experiments at identical conditions. As a rule, empirical errors are higher than theoretical ones by a factor of three to four. The main reason of underestimation of theoretical errors is most likely the assumption of uncorrelated measurements.

Even though the assumption of uncorrelated measurements yields underestimated error values, it is a very useful theoretical approximation, allowing to compare accuracy of analysis under different experimental conditions as well as different methods of analysis. Also, this approximation provides an easy method of data simulation which is a useful tool in general. A simple and very fast method of data simulation is calculation of the expected event number as a function of photon count numbers and addition of random Poisson noise to each event number independently.

In Table 2 theoretical errors of one-dimensional and two-dimensional fluorescence intensity distribution analysis according to the present invention are presented in two selected cases of two fluorescent species. In both cases the ratio of specific brightness values of the two species is three. In the case of 2D-FIDA, it is assumed that spectral sensitivities of the two detectors are tuned to different species. In both cases data collection time of 10 s, time window of 40 μs and background count rate of 1 kHz are assumed. Note that the statistical errors of the estimated parameters are significantly lower in the 2D-FIDA example.

TABLE 2

| Method | Parameter specification | Parameter value (selected) | Percent error |
|---|---|---|---|
| 1D-FIDA (according to the invention) | $c_1$ V | 0.5 | 6.6 |
|  | $c_2$ V | 0.5 | 4.9 |
|  | $q_1$ | 60 kHz | 2.2 |
|  | $q_2$ | 20 kHz | 10.2 |
| 2D-FIDA (according to the invention) | $c_1$ V | 0.5 | 1.1 |
|  | $c_2$ V | 0.5 | 1.1 |
|  | $q_{A1}$ | 60 kHz | 0.77 |
|  | $q_{A2}$ | 20 kHz | 1.2 |
|  | $q_{H1}$ | 20 kHz | 1.2 |
|  | $q_{H2}$ | 60 kHz | 0.77 |

The two-dimensional fluorescent intensity distribution analysis according to the present invention is in the following compared to the prior art moment analysis.

Factorial moments of the distribution $P(n_1,n_2)$ are defined as $$F_{kl} = \sum_{n_1, n_2} \frac{n_1! n_2!}{(n_1 - k)!(n_2 - l)!} P(n_1, n_2). \tag{31}$$

Factorial moments are related to factorial cumulants $K_{kl}$ $$K_{kl} = F_{kl} - \sum_{\substack{i,j \\ i+j>0}} C_i^{k+1} C_j^l K_{k-i, l-j} F_{ij}. \tag{32}$$

C denotes binomial coefficients. Cumulants can be expressed through concentrations and specific brightness values by a simple relation $$K_{kl} = \chi_{k+l} T^{k+l} \sum_i c_i q_{1i}^k q_{2i}^l. \tag{33}$$

If the unit of B is selected by the equation $X_1 = X_2$, $Z_1$ has the meaning of the sample volume, denoted by V, and Eq. 33 can be written as $$\gamma_{k+l} K_{kl} = \sum_i (c_i V)(q_{1i} T)^k (q_{2i} T)^l. \tag{34}$$

where $\gamma$ denotes a series of constants characterizing the brightness profile:

$$\gamma_m = \frac{\chi_l}{\chi_m}. \tag{35}$$

The principle of moment analysis is to determine values of a few cumulants from an experiment and solve a system of Eqs. 33 in respect to unknown concentrations and brightness values.

In Table 3 statistical errors of 2D-FIDA (present invention) and 2D-MAFID (prior art) are presented determined by generating a series of 30 random distributions of count numbers, simulated for identical "samples", thereafter applying 2D-FIDA and 2D-MAFID, and determining the variance of estimated parameters in both cases. Note a tendency that the advantages of 2D-FIDA compared to 2D-MAFID increase with the number of parameters to be estimated.

TABLE 3

| Data collection time, s | Number of species | Number of estimated parameters | Specification of cumulants used in MAFID | Specification of parameters | True values | Percent error of FIDA | Percent error of MAFID |
|---|---|---|---|---|---|---|---|
| 2 | 1 | 3 | $K_{01}$ | $cV$ | 0.5 | 1.1 | 1.3 |
|   |   |   | $K_{10}$ | $q_A$ | 60 kHz | 1.2 | 1.5 |
|   |   |   | $K_{11}$ | $q_B$ | 40 kHz | 1.3 | 1.6 |
| 10 | 2 | 4 | $K_{01}$ | $c_1 V$ | 0.5 | 1.1 | 2.5 |
|   |   |   | $K_{10}$ | $c_2 V$ | 0.5 | 1.0 | 4.2 |
|   |   |   | $K_{02}$ | $q_{A1}$ | 60 kHz | 0.70 | 1.2 |
|   |   |   | $K_{20}$ | $q_{A2}$ | 20 kHz | (fixed) | (fixed) |
|   |   |   |   | $q_{B1}$ | 40 kHz | 1.3 | 5.7 |
|   |   |   |   | $q_{B2}$ | 80 kHz | (fixed) | (fixed) |
| 10 | 3 | 5 | $K_{01}$ | $c_1 V$ | 0.2 | 2.0 | 2.4 |
|   |   |   | $K_{10}$ | $c_2 V$ | 0.2 | 1.2 | 1.2 |
|   |   |   | $K_{02}$ | $c_3 V$ | 0.2 | 1.6 | 1.9 |
|   |   |   | $K_{11}$ | $q_{A1}$ | 40 kHz | 1.4 | 1.8 |
|   |   |   | $K_{20}$ | $q_{A2}$ | 20 kHz | (fixed) | (fixed) |
|   |   |   |   | $q_{A3}$ | 60 kHz | (fixed) | (fixed) |
|   |   |   |   | $q_{B1}$ | 10 kHz | 3.6 | 9.0 |
|   |   |   |   | $q_{B2}$ | 60 kHz | (fixed) | (fixed) |
|   |   |   |   | $q_{B3}$ | 70 kHz | (fixed) | (fixed) |
| 10 | 2 | 6 | $K_{01}$ | $c_1 V$ | 0.5 | 1.1 | 4.3 |
|   |   |   | $K_{10}$ | $c_2 V$ | 0.5 | 1.0 | 5.0 |
|   |   |   | $K_{02}$ | $q_{A1}$ | 60 kHz | 0.70 | 1.4 |
|   |   |   | $K_{11}$ | $q_{A2}$ | 20 kHz | 1.3 | 4.5 |
|   |   |   | $K_{20}$ | $q_{B1}$ | 40 kHz | 0.90 | 2.9 |
|   |   |   | $K_{21}$ | $q_{B2}$ | 80 kHz | 0.55 | 1.5 |

Error values are calculated from the scattered results of analysis applied to a series of simulated data.

In Table 4 the relative deviation of mean values (i.e. bias) of estimated parameters are presented for 2D-FIDA (present invention) and 2D-MAFID (prior art). In each case bias is determined from analysis of a series of thirty simulated random distributions of count numbers. Three cases were analysed. In the first case, models used in data simulations and data analysis were identical. In the second case, the distributions of count numbers were simulated assuming that particles of the second species are not equivalent but being distributed by their individual brightness with a relative half-width of 20 percent. This phenomenon was intentionally ignored in analysis, however. Of course, applying a slightly inadequate model for analysis produces bias of estimated parameters. The third case is similar to the second one except the relative half-width of the individual brightness distribution of the second species is 50 percent, which is a usual value for vesicular preparations. It is worth noting that methodological deviations are noticeable when mapping weighted residuals of 2D-FIDA in cases two and three, but 2D-FIDA still returns meaningful results, 2D-MAFID is a more sensitive method to model roughness.

BRIEF DESCRIPTION OF FIGURES

The file of this patent contains at least one drawing executed in color. Copies of this patent with color drawing(s) will be provided by the Patent and Trademark Office upon request and payment of the necessary fee.

TABLE 4

| Parameter specification | True value (selected) | Bias of 2D-FIDA, percent | | | Bias of 2D-MAFID, percent | | |
|---|---|---|---|---|---|---|---|
| | | Case 1 | Case 2 | Case 3 | Case 1 | Case 2 | Case 3 |
| $c_1 V$ | 1.0 | +0.1 ± 0.2 | −0.35 | −2.0 | +0.1 ± 0.2 | −6.5 | −28 |
| $c_2 V$ | 0.05 | +0.6 ± 0.4 | −2.0 | −10.6 | +1.8 ± 0.6 | −15.6 | −69 |
| $q_{A1}$ | 20 kHz | −0.1 ± 0.2 | +0.8 | +5.0 | −0.3 ± 0.3 | +10.0 | +58 |
| $q_{A2}$ | 100 kHz | −0.3 ± 0.4 | −0.7 | −11.2 | −0.9 ± 0.3 | +5.5 | +41 |
| $q_{B1}$ | 1 kHz | −1.2 ± 0.5 | +2.6 | +20.6 | −6.7 ± 3.0 | +75 | +563 |
| $q_{B2}$ | 200 kHz | −0.3 ± 0.4 | +1.2 | +1.3 | −0.9 ± 0.3 | +11.6 | +99 |

Figure 7:
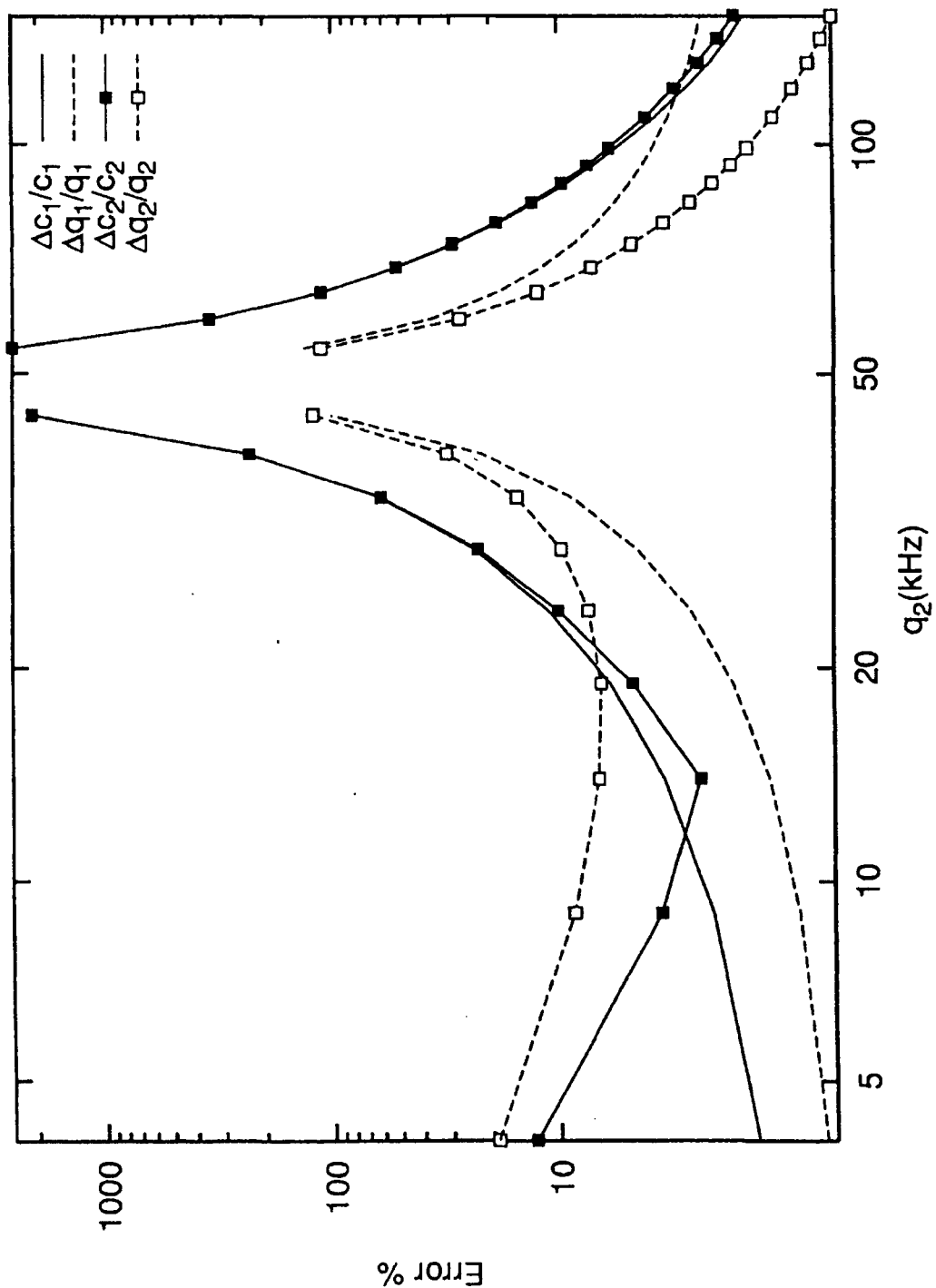

FIG. 7 illustrates theoretical errors of the estimated parameters c and q of a mixture of two species, depending on the ratio of $q_2$ to $q_1$.

Figure 8:
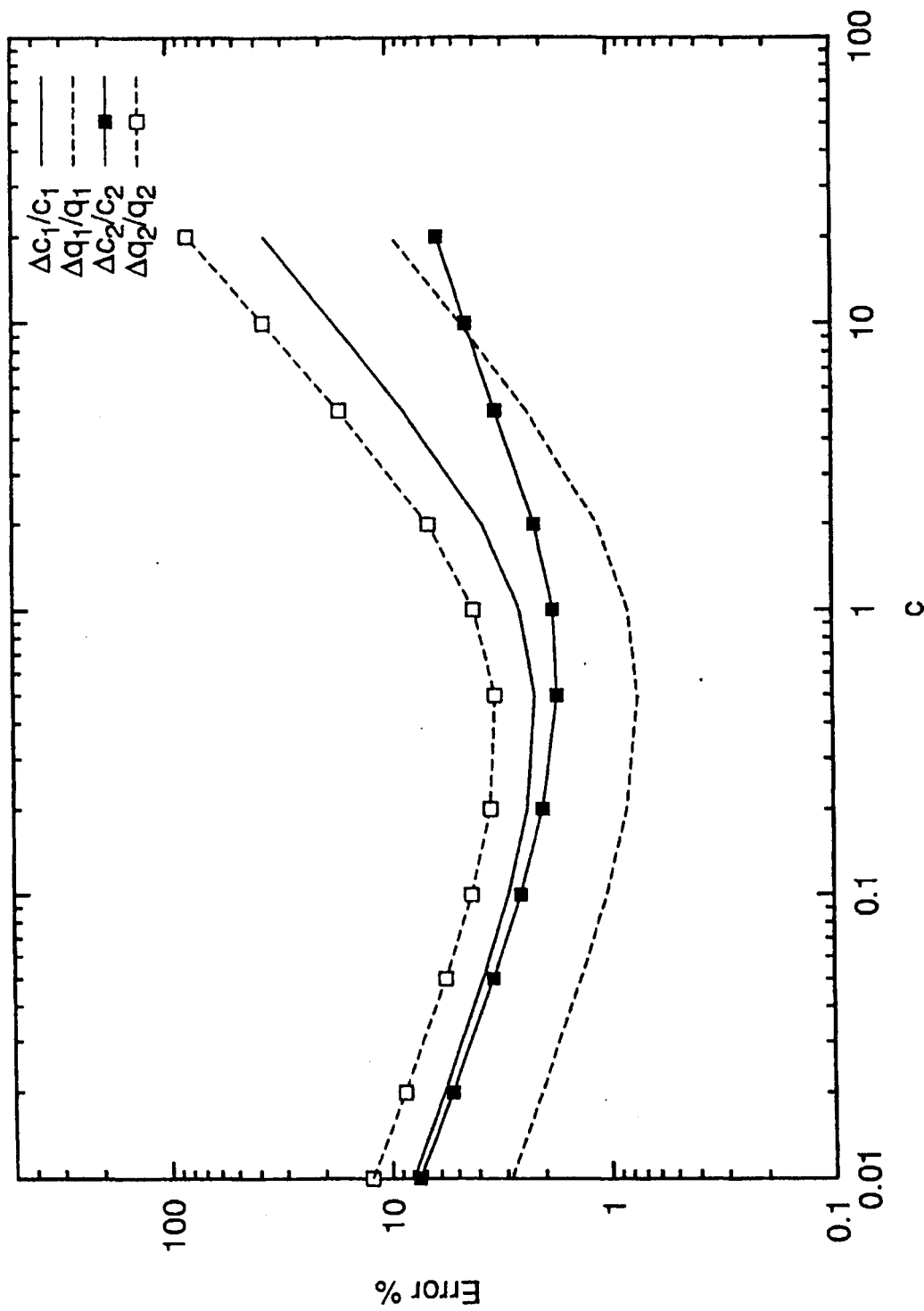

FIG. 8 illustrates theoretical errors of the estimated parameters c and q of a mixture of two species, depending on concentrations.

Figure 9:
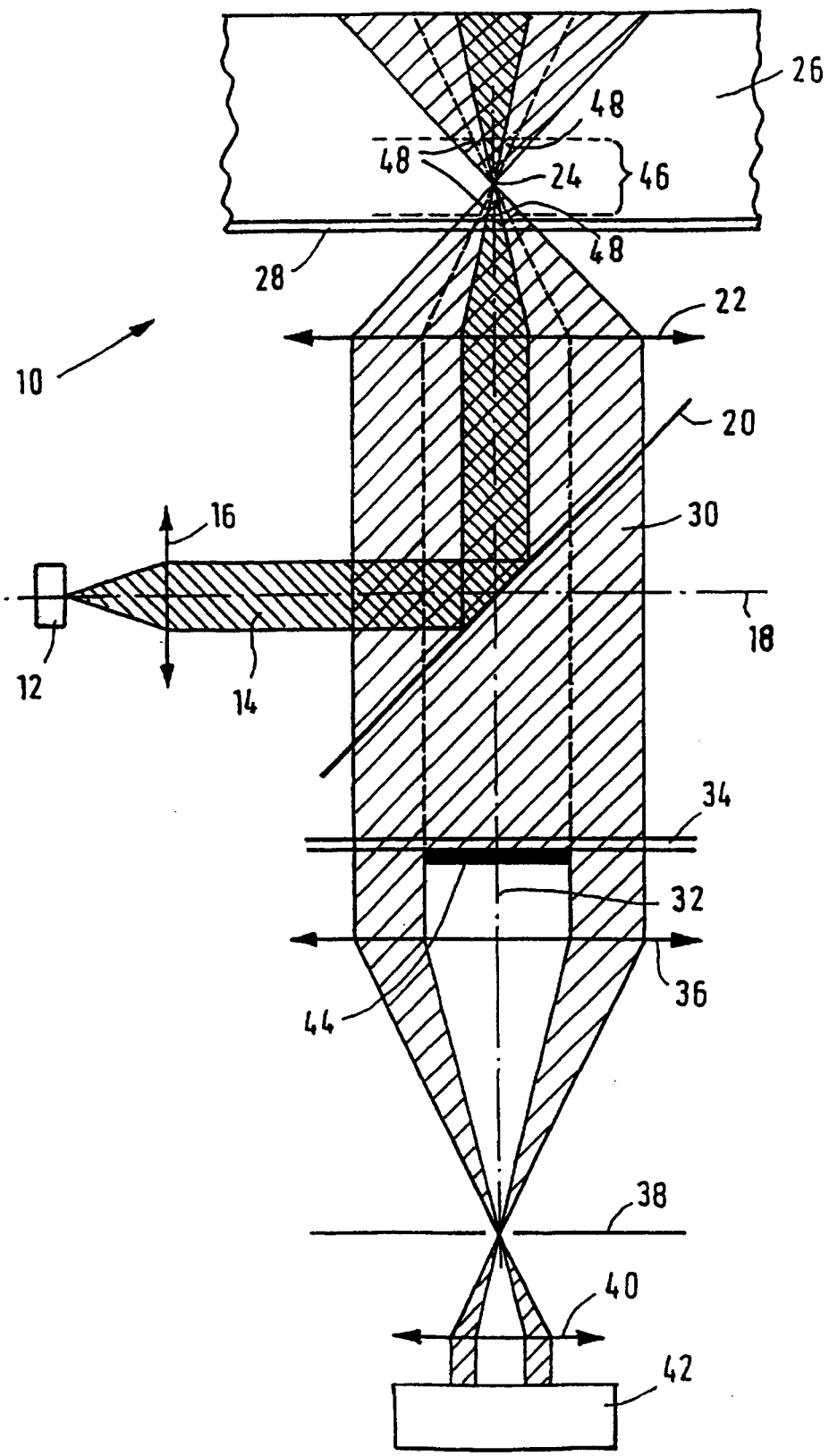

FIG. 9 illustrates in apparatus adapted for use in performing the method according to the present invention.

Figure 10A:
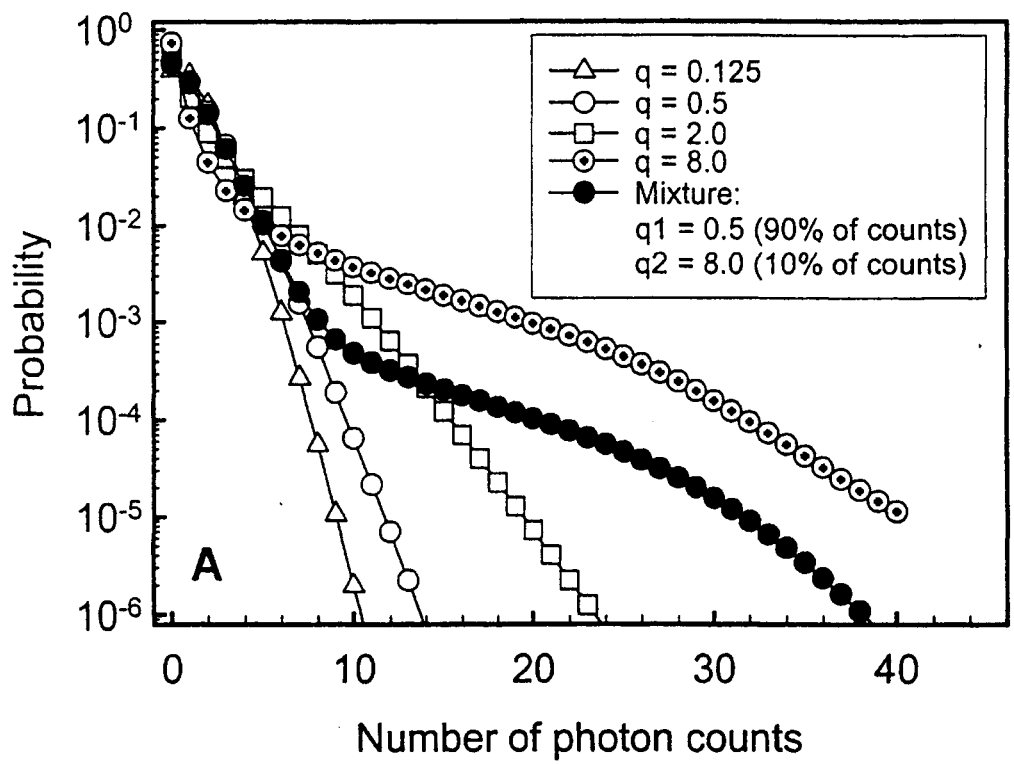

In FIG. 10A, the calculated photon count number distributions, P(n), for cases having identical mean count number $\bar{n}$ if but differing by the composition of the sample are plotted.

Figure 10B:
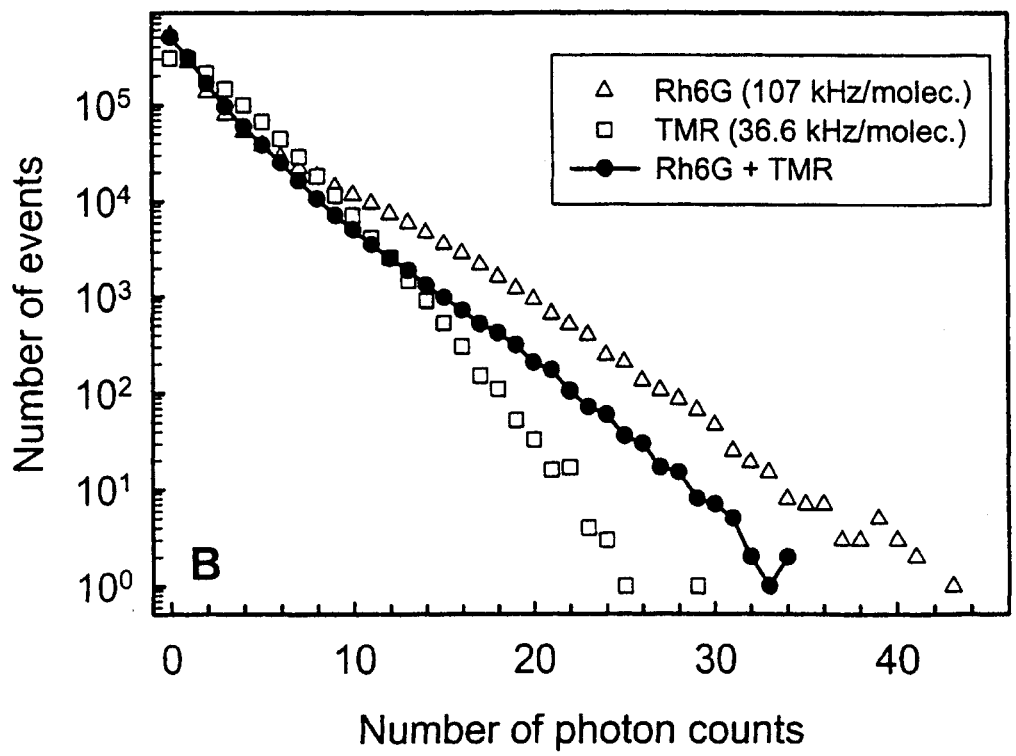

FIG. 10B illustrates the distributions of the number of photon counts of pure solutions of rhodamine 6G (Rh6G) and tetramethylrhodamine (TMR), as well as a mixture of these two dyes.

Figure 10C:
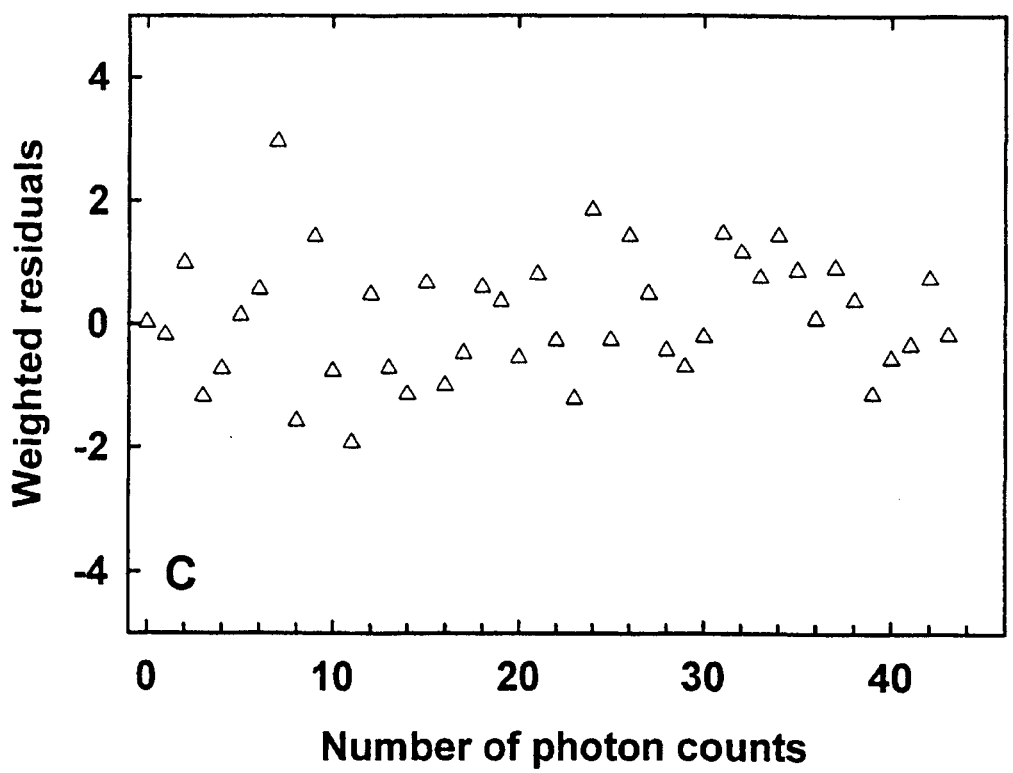

The exemplary residuals for Rh6G are shown in FIG. 10C.

Figure 10D:
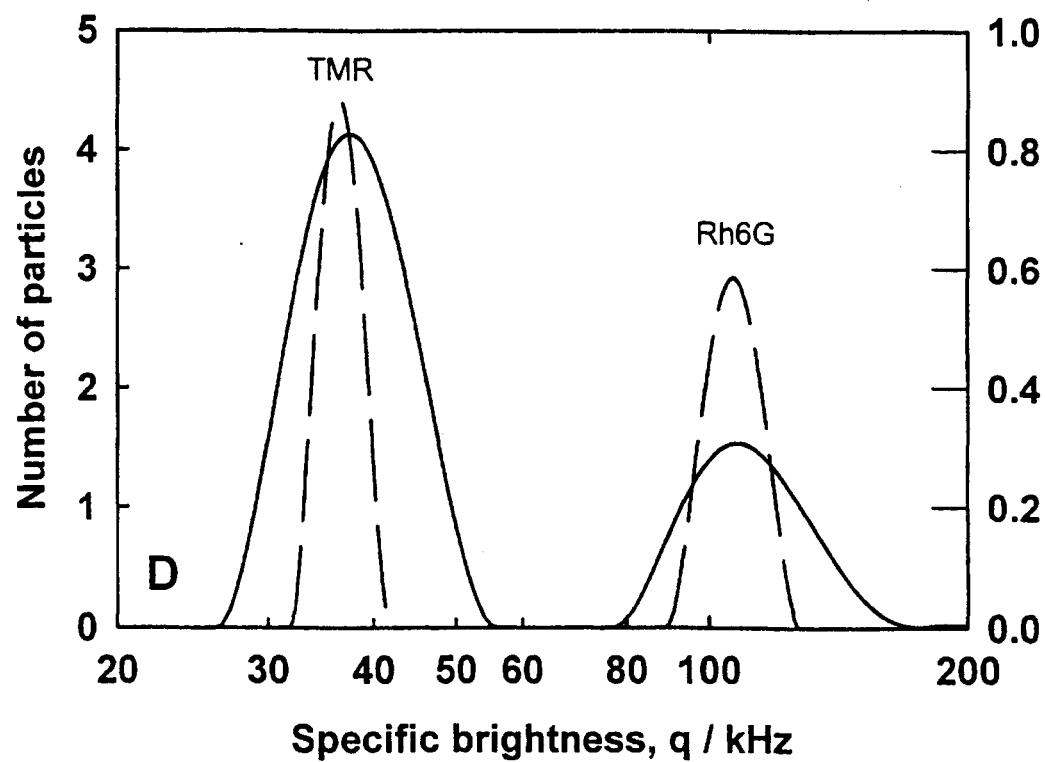

FIG. 10D shows the results of an ITR analysis (inverse transformation with the help of linear regularization and constraining concentrations to non-negative values) applied to the curves of FIG. 10B.

Figure 11:
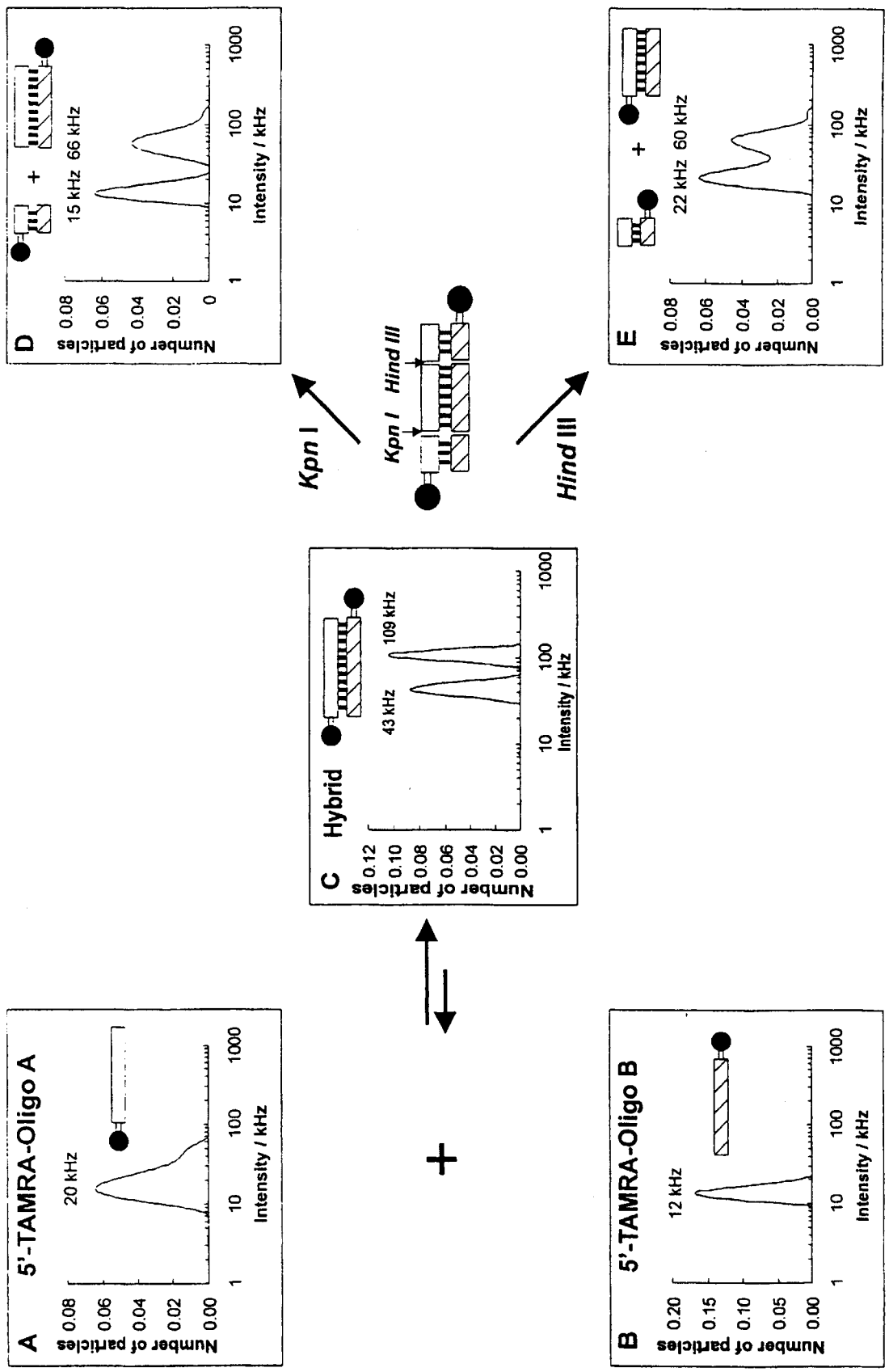

FIG. 11 shows an (TMR), analysis of hybridized (A–C) and restriction enzyme cleaved (D,E) labeled oligonucleotides. The curves result from a set of 20 individual 10 s measurements which show variations among each other of less than 10%.

FIG. 12 illustrates hybridization and restriction enzyme cleavage of different combinations of labeled and unlabeled oligonucleotides.

Figure 13:
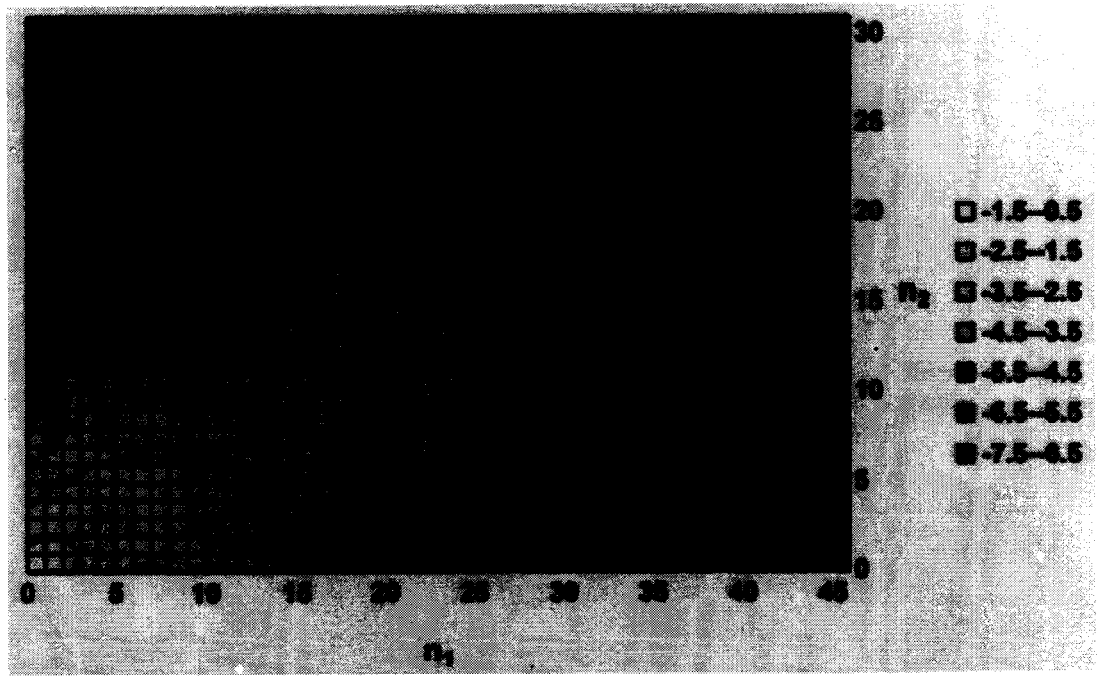

FIG. 13 is a graphical presentation of a joint distribution of the number of photon counts measured for a solution of TAMRA.

Figure 14A:
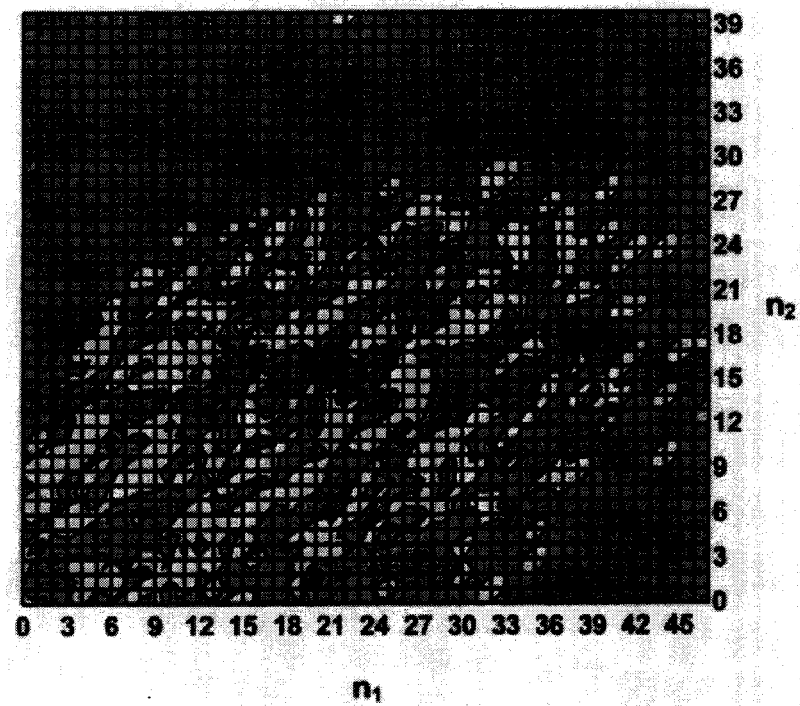
Figure 14B:
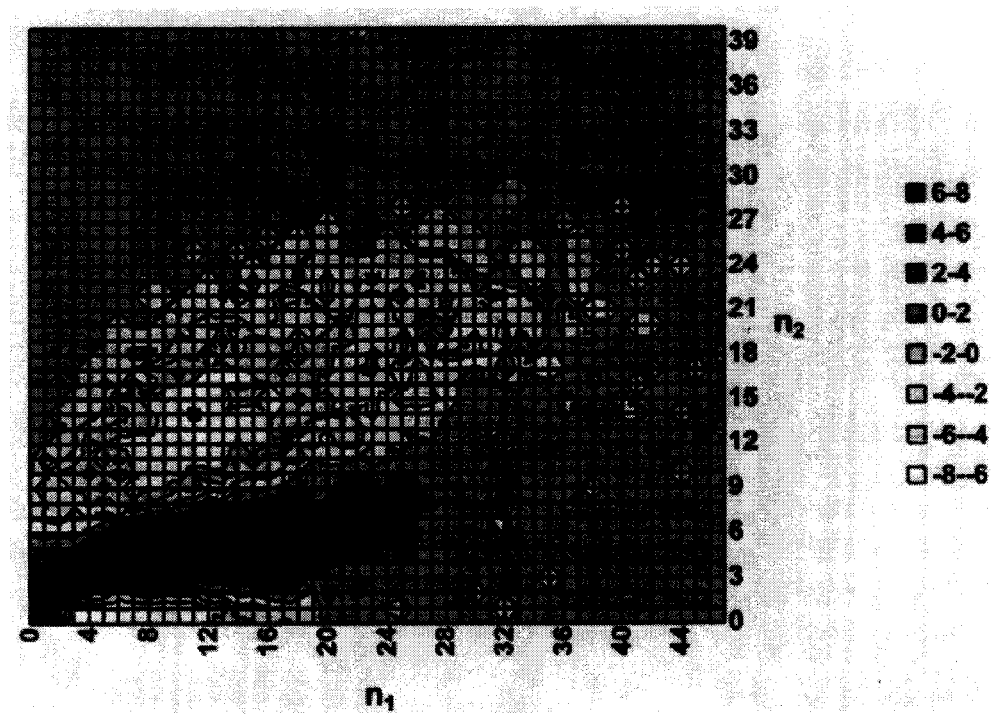

FIG. 14 is a graphical presentation of weighted residuals of a joint distribution of count numbers obtained from a mixture of TAMRA (5'-(6'-carboxytetramethylrhodamine) and RRX (rhodamine red X).

Figure 15A:
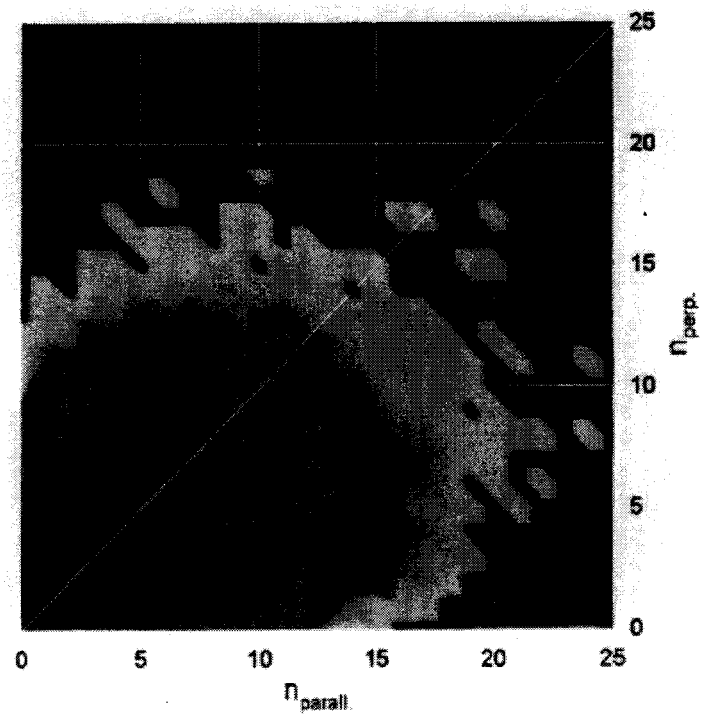
Figure 15B:
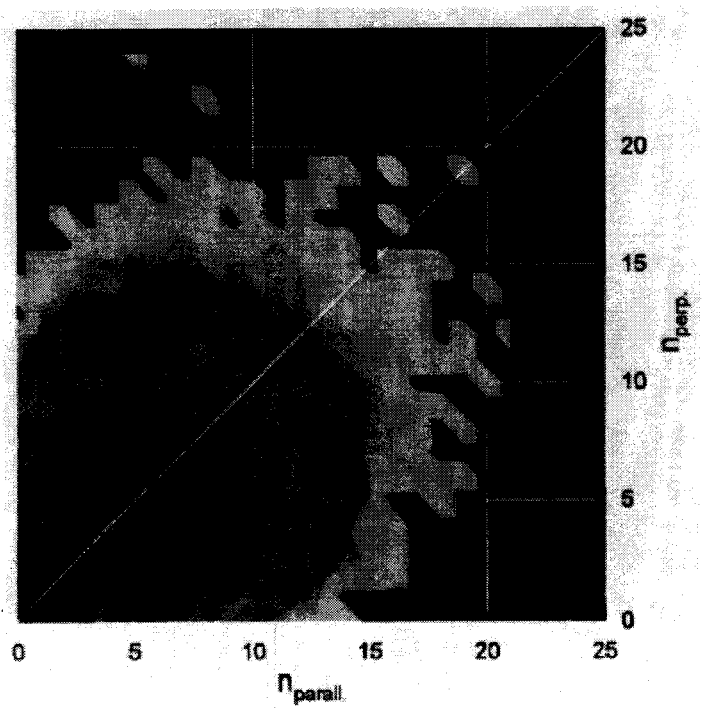

FIG. 15 illustrates joint distributions of the numbers of photon counts for the "parallel" and "perpendicular" polarization components of fluorescence measured for equal theophylline concentration of 2 nM, but different antibody concentrations.

Figure 16:
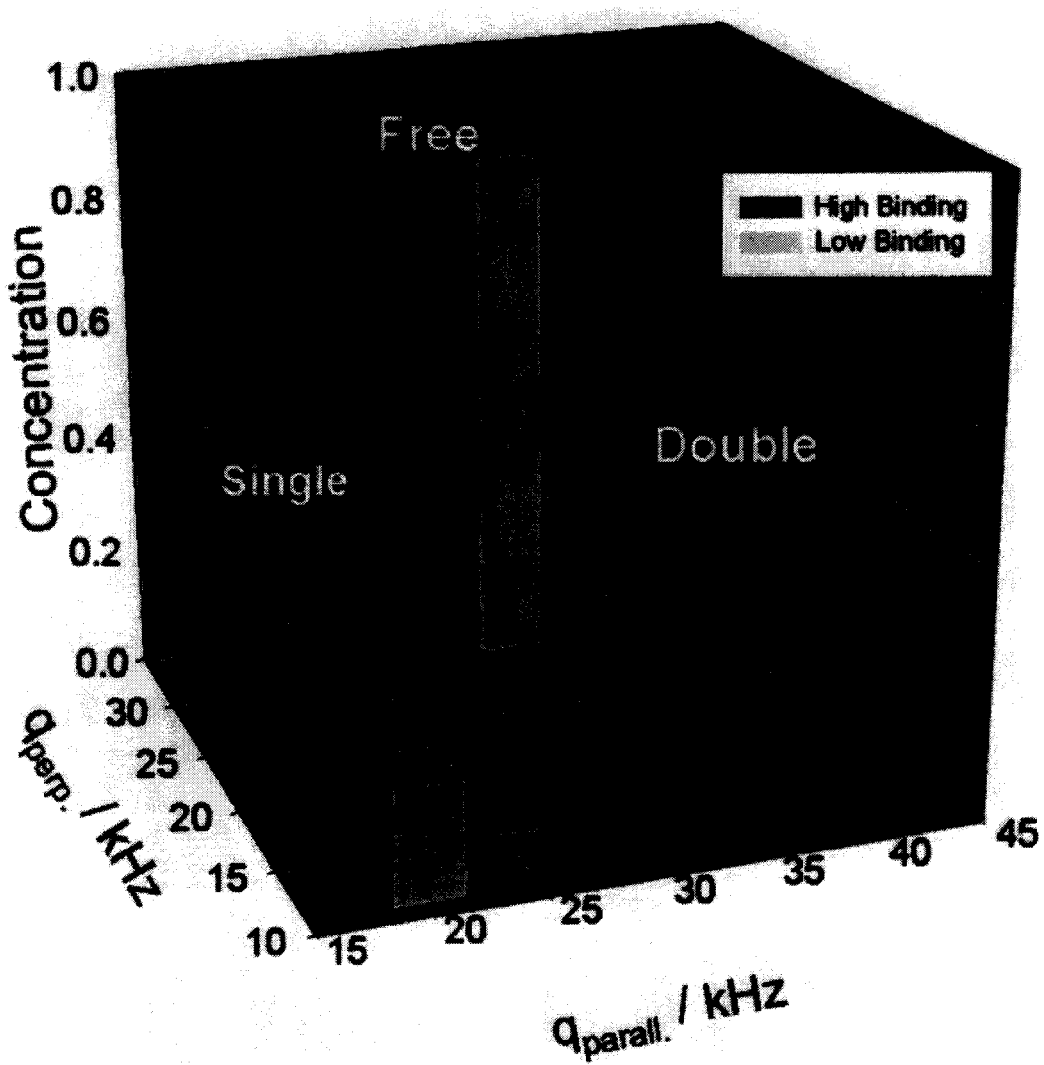

FIG. 16 illustrates the results of 2D-FIDA applied to data from samples of equal theophylline concentration, but different antibody concentration.

Figure 17:
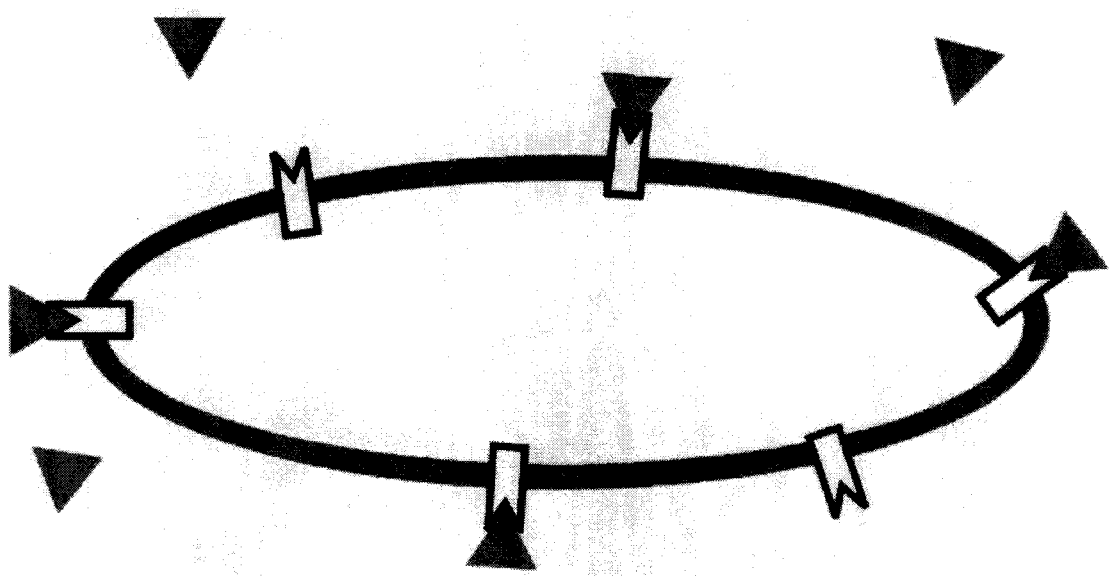

FIG. 17 Illustrates the principle of a two-color 2D-FIDA experiment with multiple binding sites per vesicle.

FIG. 18 illustrates joint distributions of the, numbers of photon counts in "green" and "red" measured in conditions of high (A) and low (B) degree of binding of SMS-14 (somatostatin-14) to SSTR-2 (human type-2 high-affinity somatostatin receptor).

Figure 19:
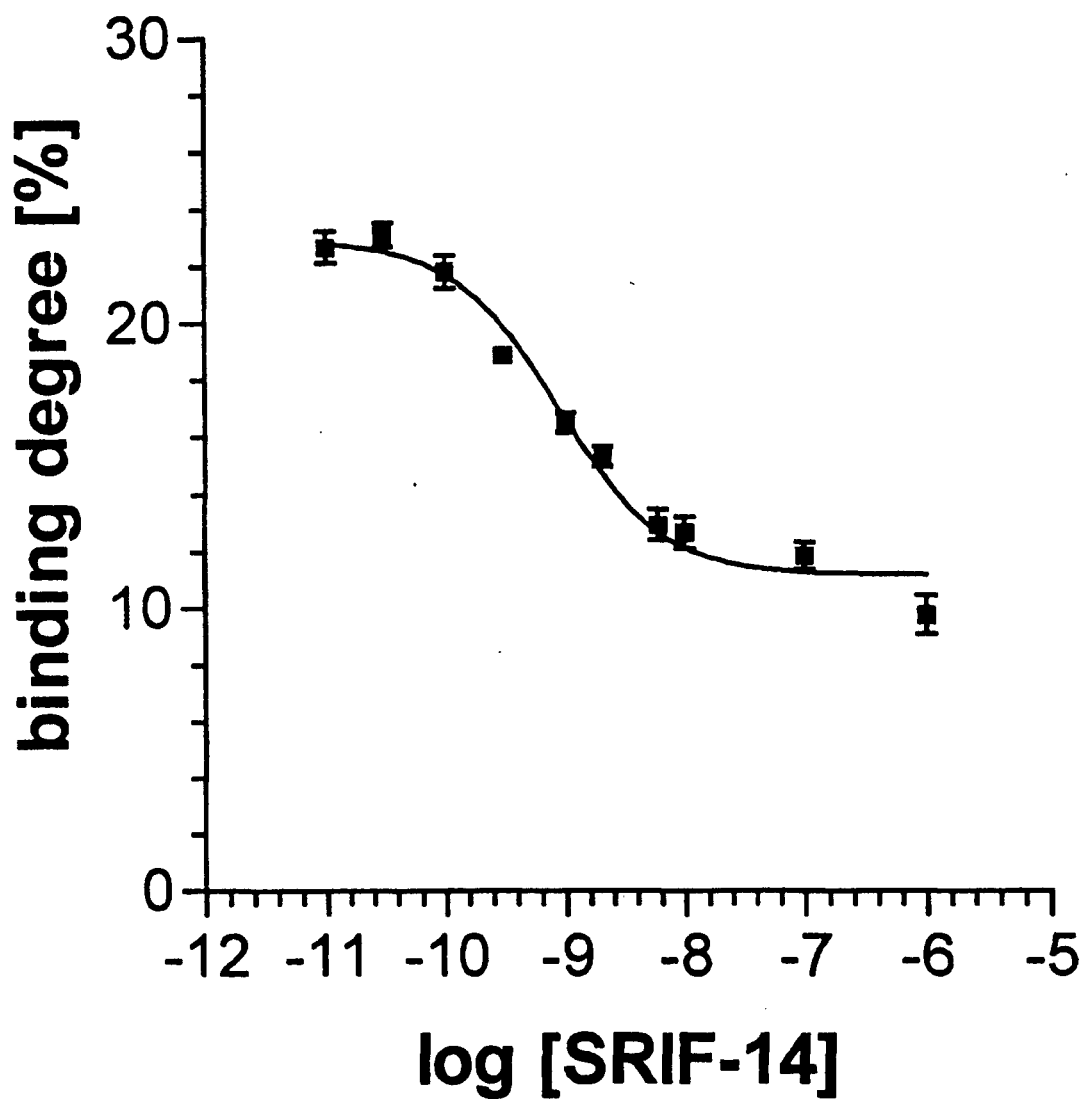

FIG. 19 shows the competition curve of the binding reaction of SMS-14 to SSTR-2.

Figure 20:
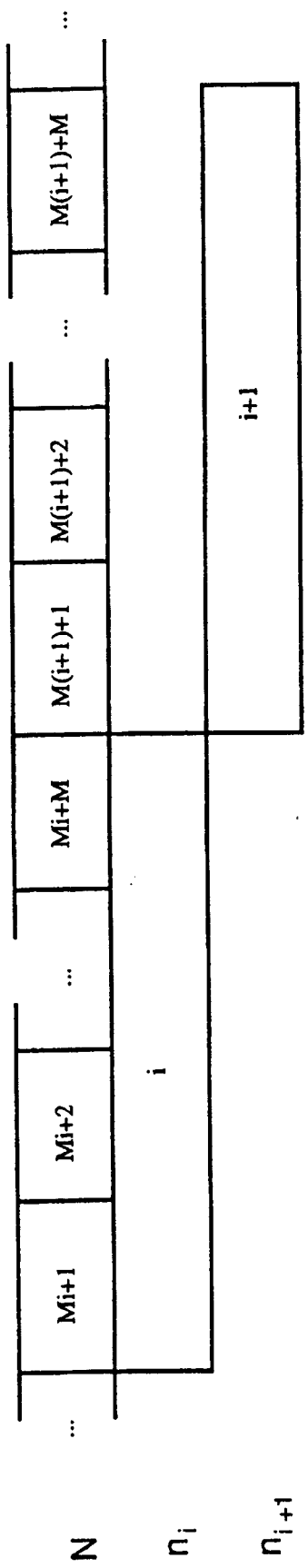

FIG. 20 illustrates an embodiment in which numbers of photon counts $\{n_i\}$ subject to determination of a distribution function $\hat{P}(n)$, in step b) are derived from numbers of photon counts in primary time intervals $\{N_j\}$ by addition of numbers of photon counts from primary time intervals according to a predetermined rule.

Figure 21:
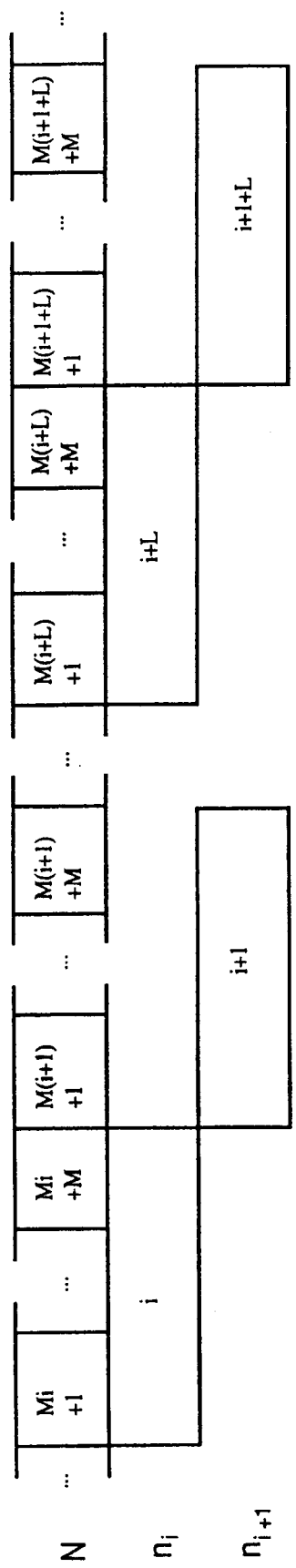

FIG. 21 illustrates a further embodiment in which numbers of photon counts $\{n_i\}$ are derived from predetermined primary time intervals according to a rule in which primary time intervals are separated by a time delay.

DETAILED DESCRIPTION OF FIGURES

Figure 1A:
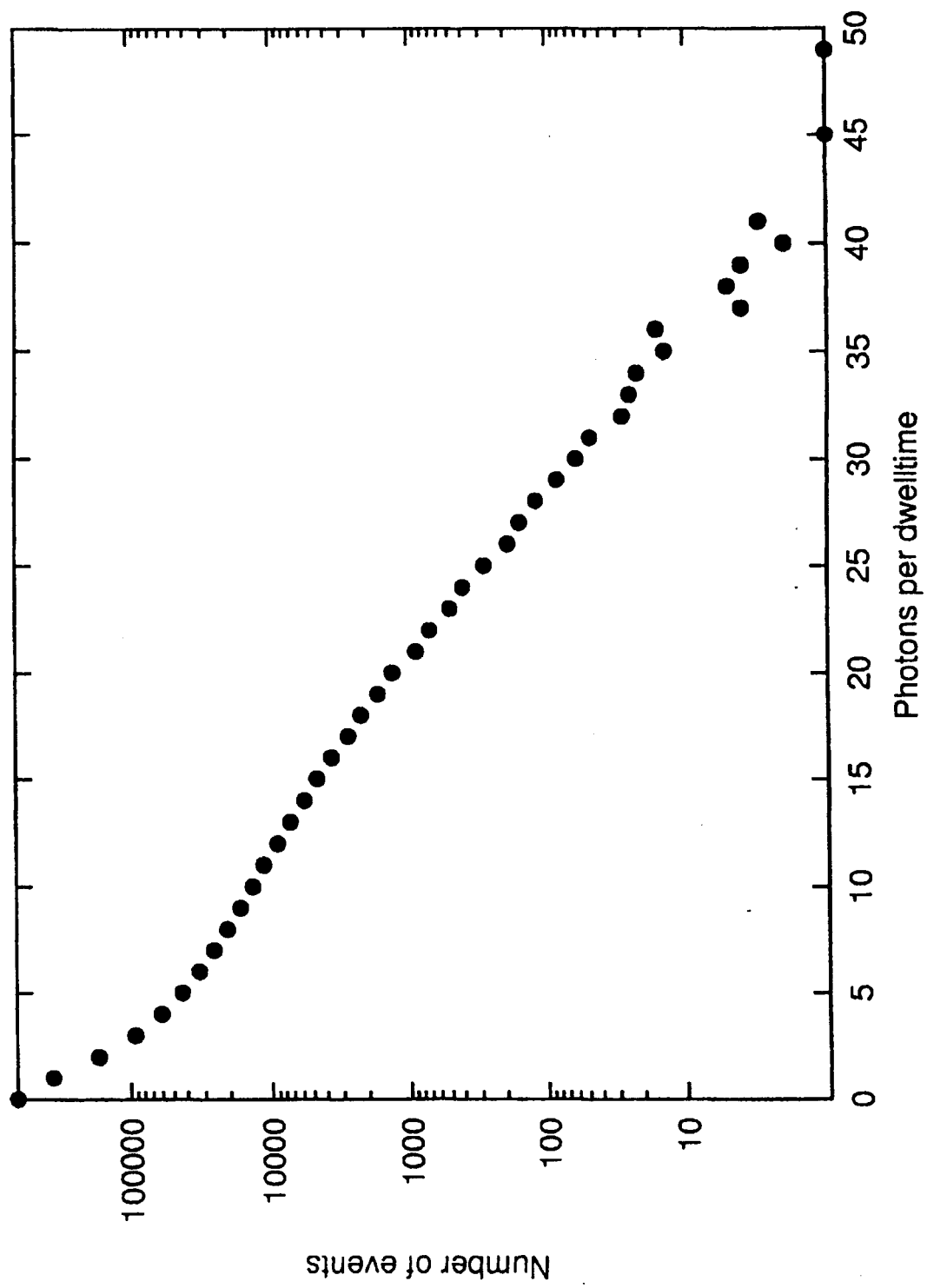
FIG. 1 shows a count number distribution obtained for a solution of the dye tetramethylrhodamine (a) and residual curves corresponding to different fitting procedures (b).
Figure 1B:
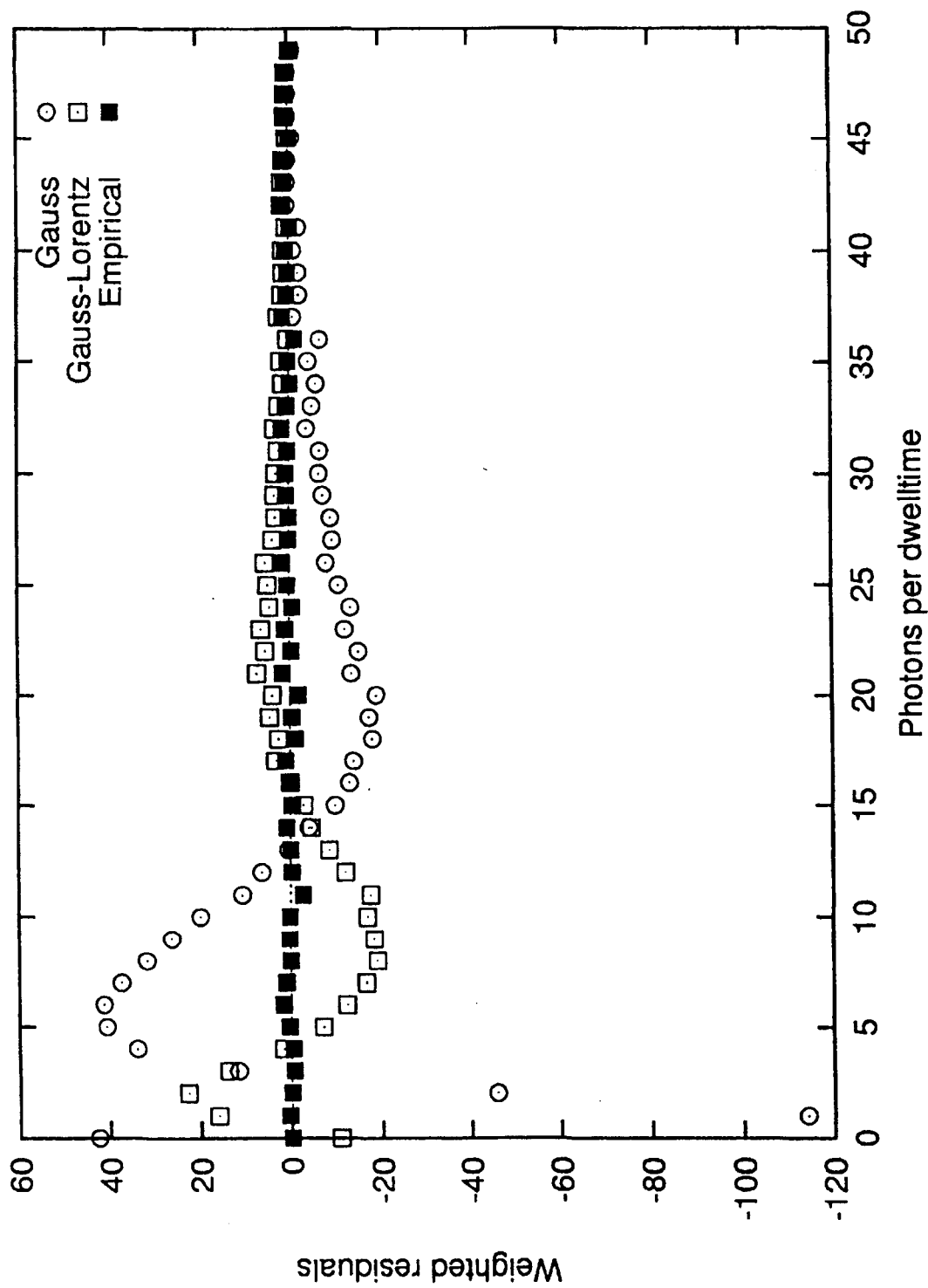

Reference is now made to FIG. 1 which shows a count number distribution obtained for a solution of the dye tetramethylrhodamine (a) and three residuals curves corresponding to the best fit obtained with Eqs (36), (37), and (38) below (b). The concentration of the aqueous tetramethylrhodamine solution was about $10^{-9}$M. Primary time intervals were 40 μs. The data collection time was 60 s.

The most widely used spatial profile model in FCS is the three-dimensional Gaussian profile with a single parameter of shape, the axial dimension ratio in longitudinal and radial directions. Residuals curve with open circles illustrates the fit quality obtainable with the Gaussian profile. There are large systematic deviations in residuals. What is a sufficiently flexible model for fitting FCS data has turned out to be a rather inflexible and inadequate model for FIDA.

A model of the sample profile which has yielded a better fit of the measured distribution $\hat{P}(n)$ is Gaussian-Lorentzian (open squares), but this model still lacks flexibility. According to Eq. (8), a certain function of the spatial brightness B is integrated over the volume. In other words, it is a relationship between B and V, characterizing a given spatial brightness profile in FIDA. For example, the Gaussian profile yields the relationship $$\frac{dV}{dx} \propto \sqrt{x}, \tag{36}$$

where x=–ln B. The Gauss-Lorentzian profile yields the relationship $$\frac{dV}{dx} \propto e^{x/4}\sqrt{\sinh\frac{x}{2}}. \tag{37}$$

Both of the relationships are rather inflexible, i.e., they do not provide any spatial shape parameters to adjust the theoretically calculated distribution to fit the measured data.

When looking for sufficiently flexible models to fit experimental data, it might be useful to apply the following relationship:

$$\frac{dV}{dx} \propto (x + a_1 x^2 + a_2 x^3). \tag{38}$$

There is a formal rather than a physical model behind Eq. (38). The fit quality obtainable with Eq. (38) is illustrated by the filled squares curve.

Figure 2:
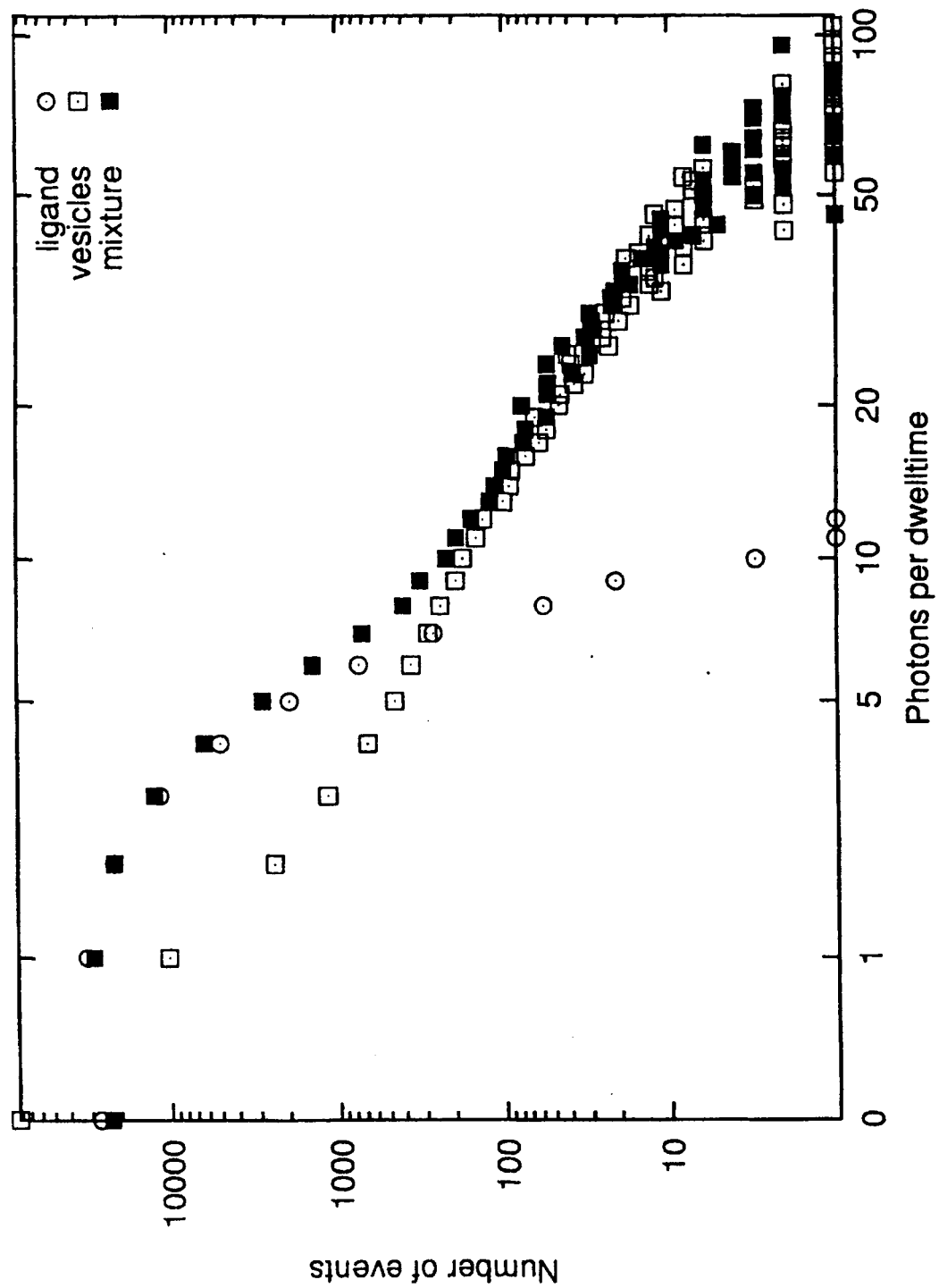
FIG. 2 shows simulated distributions of the number of counts for a case which models a binding reaction of a labeled ligand to vesicles.

Referring now to FIG. 2, simulated distributions of the number of counts an shown for a case which models a binding reaction of a labeled ligand to vesicles. Primary time intervals were 40 μs, values of the spatial parameters of Eq. (38) $a_1$=–0.4; $a_2$=0.08, background count rate b=1.0 kHz, data collection time 4 s. Curve "ligand" corresponds to a species of c=6.0; q=6.0 kHz/particle; σq=0. Curve "vesicles" corresponds to a species of c=0.05; q=300.0 kH/particle; $\sigma_q$=0. Curve "mixture" corresponds to their mixture. Concentrations and specific brightness values have been selected to model a characteristic situation in drug screening. Fining of curve (c) returns the values of the five parameters characterizing the given "sample" with statistical errors which are mostly between 3.5 and 6 percent except the error of $\sigma_q$ of vesicles which is 13 percent. If, however, $\sigma_q$ of vesicles is fixed in fitting, all the statistical errors are below 4 percent.

For the fastest, data simulation algorithm, one may calculate the expected distribution and generate a random Poisson number of events for each value of n independently.* As a cosmetic error, the total number of events $$\sum_n S(n)$$

may slightly deviate from the pre-given number M. A slower but a straightforward data simulation algorithm is the generation of a random configuration of particles in volume elements contributing to fluorescence, the calculation of the classical light intensity corresponding to the given configuration of particles, and the generation of a random Poisson number corresponding to this intensity, as a simulated number of photon counts. This procedure is repeated M times to obtain a simulated count number distribution.

*Generation of a random Poisson number is the following. For a given expected value of events E, a simulated number of events S is determined from a routinely generated random number R between 0.0 and 1.0 through inequations $$\sum_{i=0}^{S-1} \text{Poisson}(i; E) < R \leq \sum_{i=0}^{S} \text{Poisson}(i; E).$$

Figure 3:
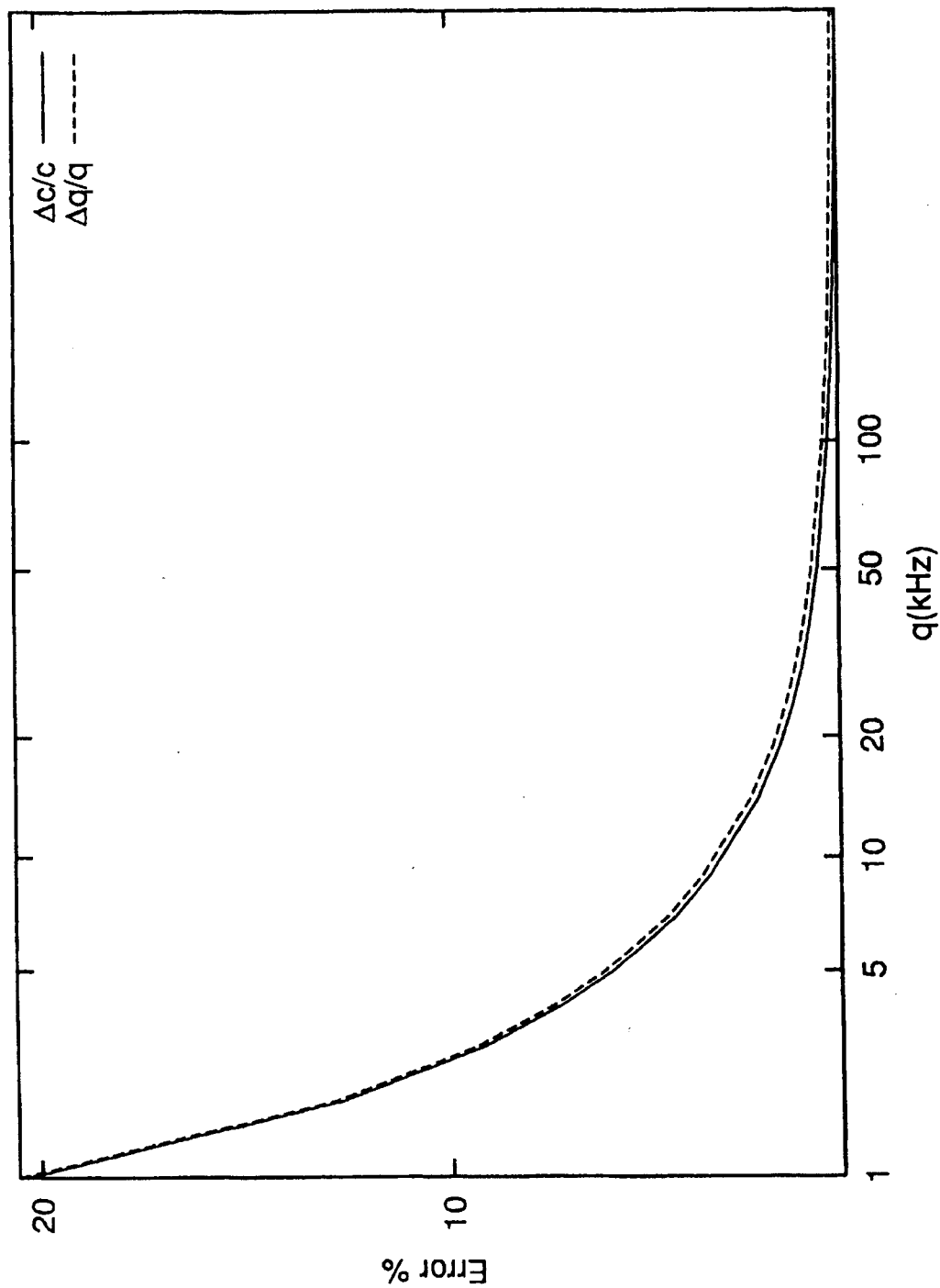
FIG. 3 illustrates theoretical errors of the estimated parameters c and q of a solution of single species, depending on the value of q.

Reference is now made to FIG. 3 which illustrates the theoretical errors of the estimated parameters c and q of a solution of single species, depending on the value of q. The following values of experimental parameters were selected: c=1.0; T=20 μs; $a_l$=−0.4; $a_2$=0.08; b=1.0 kHz; data collection time 2 s.

Figure 4:
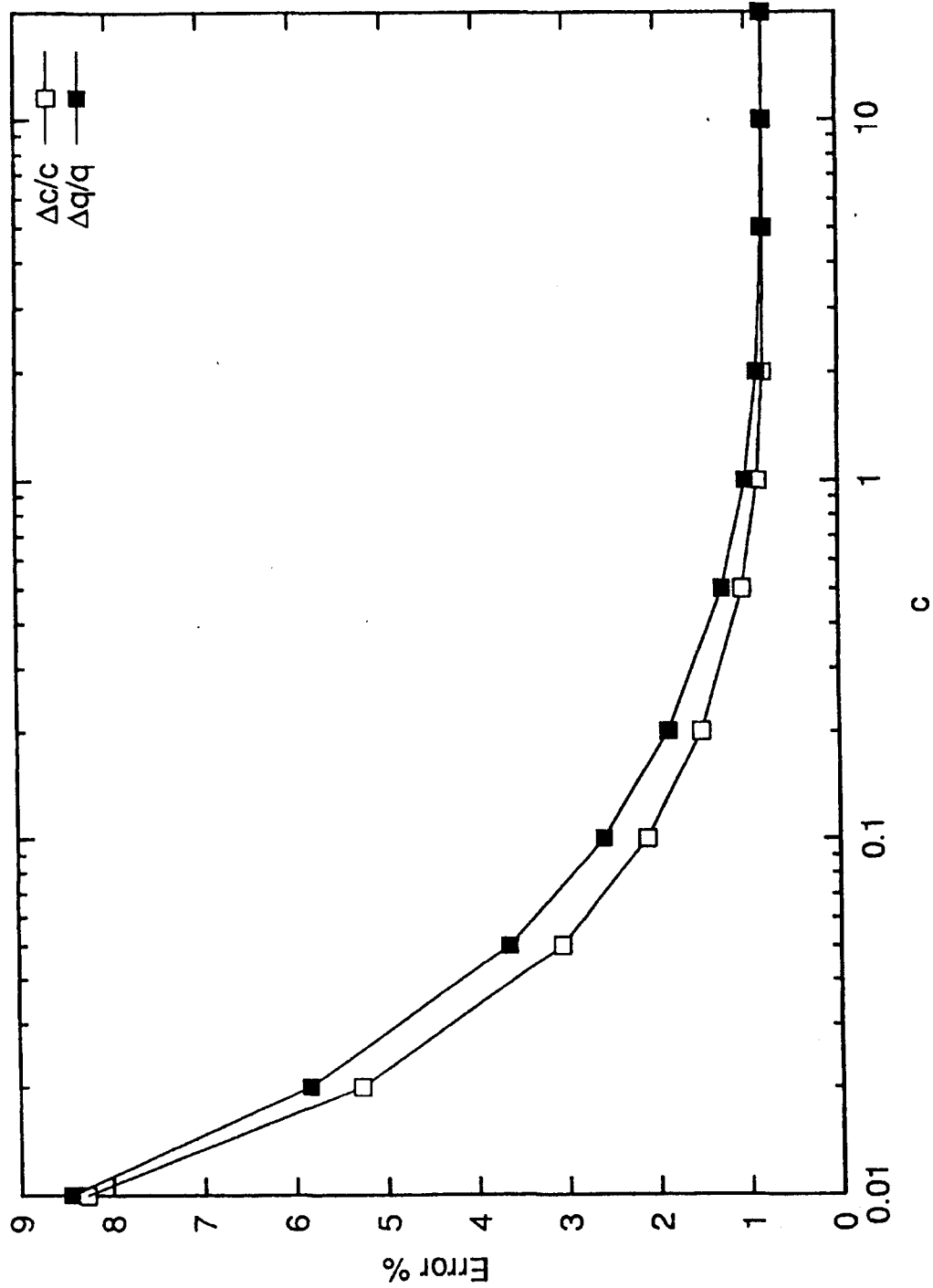
FIG. 4 illustrates theoretical errors of the estimated parameters c and q of a solution of single species, depending on the value of c.

FIG. 4 illustrates the theoretical errors of the estimated parameters c and q of a solution of single species, depending on the value of c. The following values of experimental parameters were selected: q=60 kHz/particle; T=20 μs; $a_2$=−0.4; $a_1$=0.08; b=1.0 kHz; data collection time 2 s.

Figure 5:
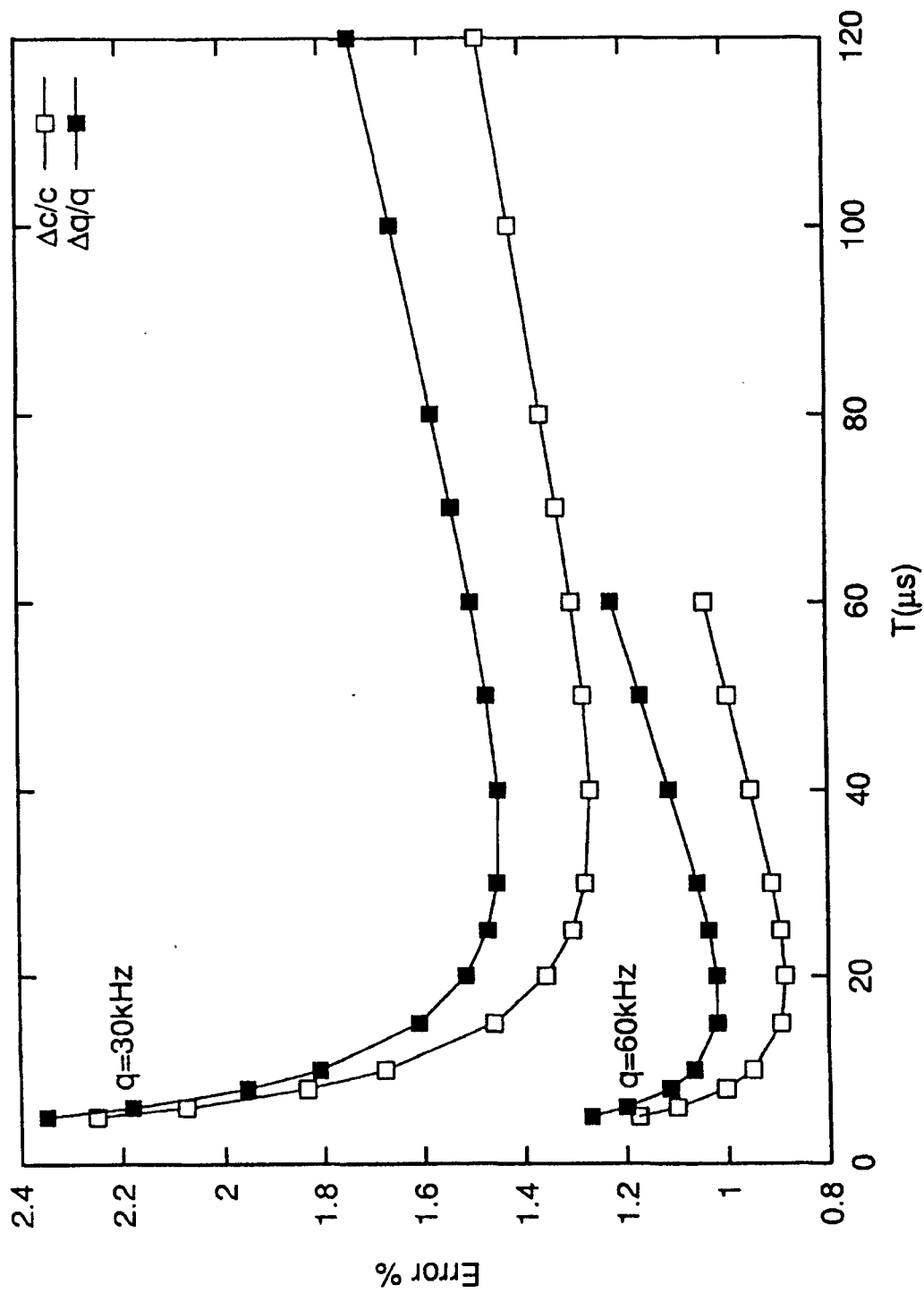
FIG. 5 illustrates theoretical errors of the estimated parameters of c and q of a solution of single species, depending on the value of T.

Referring now to FIG. 5, theoretical errors of the estimated parameters c and q of a solution of single species are shown, depending on the value of T. The following values of experimental parameters were selected: c=1.0; q=30.0 kHz/particle (upper graphs); q=60.0 kHz/particle (lower graphs), $a_1$=−0.4; $a_2$=0.08; b=1.0 kHz, data collection time 2 s.

Figure 6:
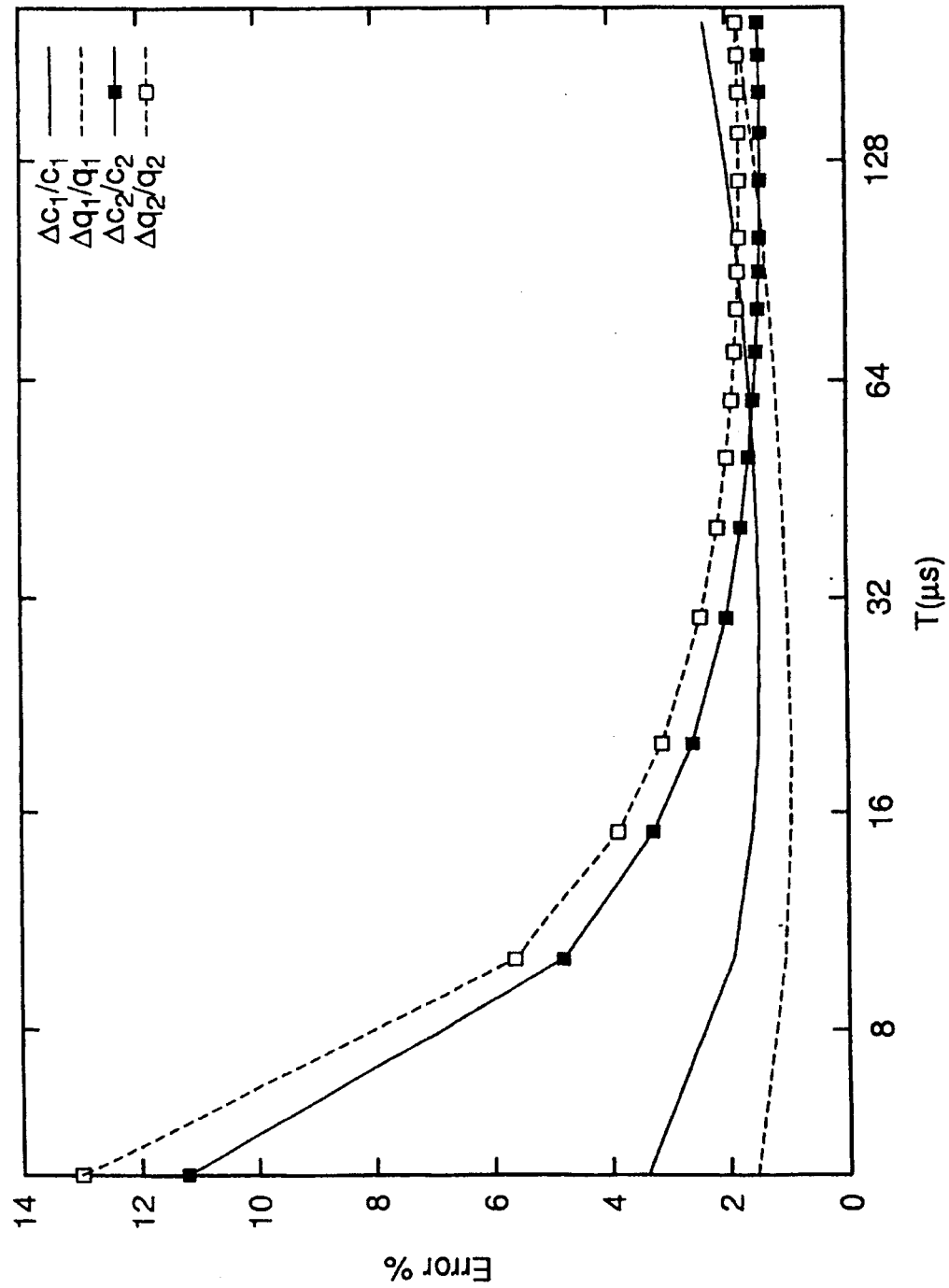
FIG. 6 illustrates theoretical errors of the estimated parameters c and q of a mixture of two species, depending on the value of T.

FIG. 6 illustrates the theoretical errors of the estimated parameters c and q of a mixture of two species, depending on the value of T. The following values of experimental parameters were selected: $c_1$=0.1; $c_2$=2.0; $q_1$=200.0 kHz/particle; $q_2$=10.0 kHz/particle; $a_1$=−0.4; $a_2$=0.08; b=1.0 kHz; data collection time 10 s. Note that the optimal value of T for the determination of the parameters of the brighter species is lower than that of the darker species.

Reference is now made to FIG. 7 which illustrates the theoretical errors of the estimated parameters c and q of a mixture of two species, depending on the ratio of $q_2$ to $q_1$. The following values of experimental parameters were selected: $q_1$=50.0 kHz/particle; $c_1$=$c_2$=0.5; $a_1$=−0.4; $a_2$=0.08; b=1.0 kHz; data collection time 40 s.

FIG. 8 illustrates the theoretical errors of the estimated parameters c and q of a mixture of two species, depending on concentrations. The concentrations were changed synchronously, $c_1$=$c_2$. The following values of experimental parameters were selected: $q_1$=75.0 kHz/particle; $q_2$=25.0 kHz/particle; $a_1$=−0.4; $a_2$=0.08; b=1.0 kHz, data collection time 60 s. Note that an optimal concentration exists at about one particle per sample volume. This is generally true, except if less than three parameters an to be determined.

Reference is now made to FIG. 9 which shows one embodiment of an apparatus adapted for use in performing the method according to the present invention. Apparatus 10 comprises a laser 12 which saves as a fight source for illuminating do sample by a bundle of coherent, monochromatic excitation radiation 14. Excitation radiation 14 is paralleled by a leas 16 and reaches a dichroic mirror 20. Preferably, the angle between the optical axes 18 and the dichroic mirror 20 is 45°. The dichroic mirror 20 reflects the excitation radiation 14 in direction of an objective lens 22 having its focus 24 within a sample, volume 26. Sample volume 26 and objective lens 22 are preferably separated from each other by a transparent cover glass 28, e. g. by the bottom of a commercially available micro-liter plate which houses the sample. The sample preferably includes fluorescently labelled molecules or other particles, Due to excitation by an appropriate excitation radiation 14, the molecules or other particles present in the sample emit radiation 30. Emission radiation 30 passes the objective lens 22 and reaches the dichroic mirror 20 which is transparent for emission radiation 30. Thereafter, emission radiation passes a filter 34 and a collimator lens 36 on the optical axes 32. A pinhole 38 is situated in the focus of collimator, lens 36. Emission radiation 30 passing the pinhole 38 reaches a further lens 40 and, thereafter, is detected by the photo-detector 42. Within the pathway of emission radiation 30, in particular between dichroic mirror 20 and photo-detector 42, an opaque means 44 is provided tough which it central part of the emission radiation 30 cannot pass. This central pan of the emission radiation 30 stems from area on the optical axes 32 in front of or behind the focus 24 of the excitation radiation 14. Only emission radiation 30 that stems from the focus 24 or its direct neighbourhood passes the pinhole 38 and reaches photo-detector 42. Instead of placing an opaque means 44 within the pathway of emission radiation 30, the pathway of excitation radiation 14 is also suitable for positioning an opaque means 44. In particular, an opaque means 44 can be positioned between laser 12 and dichroic mirror 20. Use of an opaque means 44 as described in detail herein improves the signal-to-noise ratio.

In FIG. 10A, the calculated photon count number distributions, P(n), for five cases of equal mean count rate, $\bar{n}$=1.0 are shown. The open symbols correspond to solutions of single species, but with different values of the mean count number per particle qT. The solid line is calculated for a mixture of two species, one with qT=0.5 and the other with qT=8.0. Obviously, the curves differ from each other considerably. The important point is that FIDA according to the present invention can unambiguously separate the contributions of the individual species.

Reference is now made to FIG. 10B which illustrates the distributions of the number of photon counts of pure solutions of two different dyes, 0.5 nM rhodamine 6G (Rh6G) and 1.5 nM tetramethylrhodamine (TMR), as well as a mixture of the two (0.8 nM TMR, 0.1 nM Rh6G) The main equipment is a confocal microscope (ConfoCor®; EVOTEC BioSystems and Carl Zeiss, Germany) routinely used for fluorescence correlation studies. An attenuated (to about 800 μW) beam from an argon ion laser, wavelength 514.5 nm, is focused to a spot of approximately 0.5 gm radius, which is twice the size of a spot in usual FCS experiments, and results in a diffusion time of approximately 200 μs for rhodamine 6G. The excitation intensity has generally been kept lower than or equal to a level characterized by about 15 percent amplitude of the triplet term of the auto-correlation function. Fluorescence emission is detected through a pinhole on the focal plane of the microscope using an avalanche photo-diode detector SPCM-AQ 131 (EG&G). The distributions of the number of photon counts were measured at T=40 μs dwell time. Data correction time was 50 s. These distributions serve as input data for FIDA. The results of a multi-component fit analysis are given in Table 5 below with $X^2$ values calculated according:

$$\chi^2 = \frac{\sum W_n[\hat{P}(n) - P(n)]^2}{n_p - n_{fu}}, \quad (39)$$

where $n_p$ is the length of the measured distribution $\hat{P}(n)$, and $n_{fu}$ is the number of fit parameters. In said multi-component analysis one fits the measured distribution function of number of photon counts, assuming a certain number of fluorescent species, and estimates unknown concentration and specific brightness values.

As a further example, the method according to the present invention has been applied to study the hybridization of 5'-(6-carboxytetramethylrhodamine (TAMRA))-labeled 40 mers with either labeled or non-labeled complementary oligonucleotides and the subsequent symmetrical cleavage of the DNA hybrid by the restriction endonucleases Hind III and Kpn I. The specific oligonucleotides said in this study were TAMRA-AAGAAGGGGTACCTTTGGATAAAAGAGAAG-CTTTTCCCGT(5'-TAMRA-Oligo A) and TAMRA-ACGGGAAAAGCTTCTCTTTATCCAAAGGTAC-CCCTT(5'TAMRA-Oligo B).

They were purchased in HPLC pure quality from Applied Biosystems (Weiterstadt, Germany). All measurements were

TABLE 5

| Sample | $\alpha_2$ | $\alpha_3$ | C | q (kHz) | $x^2$ |
|---|---|---|---|---|---|
| Rh6G | −0.380 ± 0.009 | 0.077 ± 0.003 | 0.461 ± 0.003 | 107.2 ± 0.8 | 0.97 |
| TMR | −0.427 ± 0.032 | 0.084 ± 0.014 | 1.517 ± 0.012 | 36.56 ± 0.29 | 0.81 |
| Mixture | −0.350 (fixed) | 0.077 (fixed) | 0.103 ± 0.012 | 109.1 ± 4.0 | 0.77 |
|  |  |  | 0.738 ± 0.011 | 37.4 ± 1.0 |  |

In all cases, the background count rate was fixed to the value of 1.05 kHz, as measured with de-ionized water, $a_2$ and $a_3$ are pre-normalization values when $a_1$ is fixed to 1.0. The theoretical, statistical errors in Table 5 correspond to theoretical weights:

$$W_n = \frac{N}{P(n) + \frac{1}{N}}. \quad (40)$$

This formula is derived under a simple assumption of N independent measurements of the number of photo counts. In reality, consecutive measurements are correlated, therefore the errors of estimated parameters returned by the fitting algorithm underestimate real statistical errors. We have empirically determined from a separate series of 30 to 200 measurement that these statistical errors are greater than theoretical ones by a factor of about three.

The exemplary residuals for Rh6G are shown in FIG. 10C.

Figures 12A, 12B:
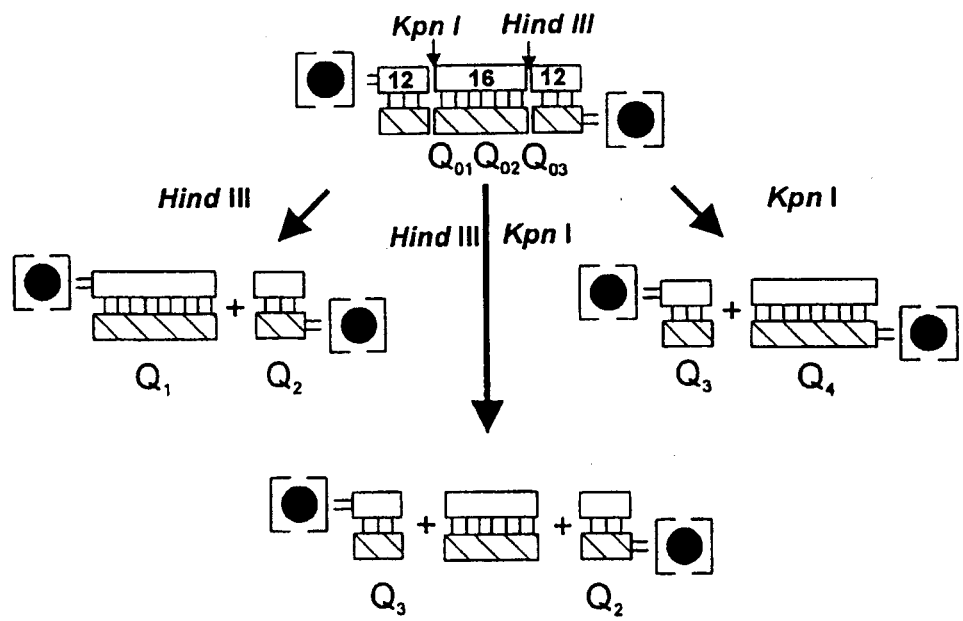

The results of ITR analysis are shown in FIG. 10D expressing the distribution of the number of particles as a function of their specific brightness. Such ITR analysis is an inverse transformation realized with the help of linear regularization and constraining concentrations to non-negative values. ITR is a valuable tool especially for samples from which either no a priori information about the sample composition is given or where the sample composition is heterogeneous. The dashed lines correspond to the solutions of the single dyes (Rh6G and TMR) and the solid line to their mixture. The ordinates give the mean number of particles within the confocal volume element (left: single dyes; right: mixture). For equipment details see description of FIG. 10B. The ideal outcome would be single δ-peaks for the solutions of single species and two δ-peaks for the mixture. In reality, the width of the ITR output spectral peaks is determined not only by the true width of the distribution of specific brightness values but also by the accuracy of input data and the particular realization of the linear regularization; simply, if a broad spectrum fits experimental data as well as a narrow one then ITR prefers the broad one.

carried out on the above described FCS reader at excitation/emission wavelength of 543/580 nm using a 4 mW helium/neon laser (Uniphase) attenuated to approximately 300 μW. The water background was found to be below 800 Hz. For the measurements, sample aliquots were diluted to 1 nM and 20 μl were assayed in a 8-well chambered coverglass (Nalge Nunc) at room temperature. The hybridization reaction was performed in 70% formamide containing 10 mM Tris/HCl buffer (pH 8.0), 1 mM EDTA, 0.2 mM NaCl and an oligonucleotide concentration of 0.5 μM. Denaturation was at 95° C. for 2 min and subsequent hybridization was at 55–60° C. for 40 min in accordance with the optimized temperature Tx which is 10–15 degrees below the melting point Tm (Heating block, Techne). Tm was calculated as follows; Tm=81.5+16.6 (log10[Na+])+0.41 (%G+C)−600/N (N=40; %G+C=42.5). Restriction digest analyses of the hybrid DNA were performed by the restriction enzymes Hind III and Kpn I. The restriction site was chosen in order to obtain fragments of different size. The cleavage reactions were performed in 3.3 mM tris/acetate (pH 7.9), 1 mM magnesium acetate, 6.6. mM potassium acetate and 0.1 mg/ml bovine serum albumin at 37° C. for 1 h. The reaction course is characterized by significant shifts of the fluorescence intensity per molecule within a range of one order of magnitude (FIGS. 11A–E). It is important to note that the resulting double product peak corresponds to one single hybridization species in which no none-hybridized species are detectable. This could be easily demonstrated in hybridization/cleavage experiments using labled/nonlabeled oligonucleotide combinations where signals with different brightness compared with the double labeled hybrid have been obtained (FIG. 12A,B). One explanation for such a double-peak structure could be conformational fluctuations resulting from transitions between two conformational states. This behavior is described using a three-state model of the conformational dynamics with a polar, a nonpolar, and a quenching environment of the label (Eggeling et al., Proc. Natl. Acad. Sci. USA 95: 1556–1561). From the present data it can be concluded that the conformational fluctuations are significantly dependent on the DNA length and the number of labels. The small digested DNA fragments exhibit a single brightness and the concentration ratio of the educt double peaks shifts toward one component when one-label hybrids are studied. As a further result, small fragments show low molecular brightness and large fragments correspond to high brightness values ($Q_2 \approx Q_3$, $Q_1 \approx Q_4$).

Based on symmetrical cleavage sites for both enzymes DNA fragments of equal size and subsequently very similar molecular brightness are to be expected. FIGS. 12A and B clearly illustrate that such a result has been observed and the theoretical relationship $Q_1+Q_2=Q_3+Q_4$ is experimentally confirmed. Restriction digest analyses of the hybrid DNA were performed with the restriction enzymes Hind III and Kpn I either alone or in combination. The restriction sites lead to symmetrically cleaved fragments (2×2 mers, 1×16 mer for double digest). [•] corresponds to labeled DNA. $Q_{Q1-Q3}$; intensities of DNA hybrids, $Q_i$; intensities of cleavage products. The bulk of all the measurements of cleavage products using single and doubly labeled DNA structures makes it possible to classify all observed intensities with individual structures in a single measurement—a property of the method of the present invention which is not possible using any other known analytical method.

Reference is now made to FIGS. 13 and 14. As the central, optical part of the equipment for 2D-FIDA, a confocal microscope is used, like in FCS spectrometers (Koppel et al., Biophys. J. 16: 1315–1329, 1976). For excitation of fluorescence, a beam from an Ar or green He-Ne laser is attenuated by neutral filters, passes a beam expander and is directed to the microscope objective by a dichroic mirror. In a number of experiments with slowly diffusing particles, beam scanning in combination with sample scanning is used, as a tool known from laser Scanning microscopy. Fluorescence is collected by the same objective through the dichroic mirror, and is focussed to a confocal pinhole which serves to reject the out-of-focus light. Resolution in the longitudinal direction is additionally improved by using a concentrical opaque spot closing about a quarter of the aperture in the fluorescence collection path of the microscope (see description of FIG. 9). The fight which passes the pinhole is divided by a beamsplitter for detection by two detectors. Depending on the general type of a 2D-FIDA experiment, the beamsplitter is either a polarization cube, or a dichroic mirror. In the first case, a common spectral band-pass filter is used, while in the case of two-colour FIDA, each detector has a different band-pass filter in front of it. The photon counting detectors are silicon avalanche photodiode modules SPCM-AQ-131, EG&O Optoelectronics, Canada. The TTL pulses from the detectors are counted by a two-channel counter, constructed by EVO-TEC BioSystems AG (Hamburg, Germany) as a plug-in card of a computer. The count number distributions are calculated during reading data from the 32 MB onboard buffer, which itself is an online process. By feeding the detector outputs to a correlator, FCS measurements can be performed in parallel with FIDA experiments.

The levels of background count rate for both detectors are determined by a separate experiment on bi-distilled water. The main contributor to the non-fluctuating background light intensity is Raman scattering from water.

The radius of the monitored sample volume can be adjusted by selecting an appropriate expansion factor of the original law beam. The focal beam radius of about 0.6 μm is used yielding diffusion times for simple organic dye molecules (e.g., TAMRA) of about 260 μs, which is considered long compared to the 40 μs, dwell time of counters, so that the approximation of constant molecular brightness during the counting interval is valid. The excitation intensity is adjusted as a compromise between a high count rate per molecule and low population of the triplet state. The triplet state population was kept at about 15 percent level. Higher triplet population values might significantly distort the apparent spatial brightness profile. The population of the triplet state was measured with the correlator (ALV-5000, ALV, Langen, Germany) during the set-up of a series of experiments.

For methodological test experiments, two different dyes were selected, carboxytetramethylrhodamine (TAMRA) and rhodamine red X (RRX). These dyes have different emission spectra, as well as different extinction coefficients at the laser wavelength of 543.5 nm. In these experiments, a wideband 40/60 beamsplitter was used in front of the detectors. The spectral filter of the "red" channel has the center wavelength of 605 nm and FWHM of 50 nm while the corresponding figures for the "yellow-green" channel are 575nm and 30 nm. The dyes were diluted in distilled water so that the average number of molecules in the observation volume was in the range of 0.5 to 2.0, corresponding to concentrations between 0.23 and 0.92 nM.

For each experiment about 20 μl of the sample solution was placed on a coverslip separating the sample from the water immersion objective (Zeiss C-Apochromat 40×1.2 W Korr). Each distribution was collected for 60 seconds. Each of the dyes was measured separately, but also mixtures of the dyes with different concentration ratios were measured. The parameters describing to spatial brightness profile were determined from an experiment on TAMRA and were fixed in subsequent analysis of other samples at values $a_1=-0.045$ and $a_2=0.0772$. Mixtures were measured and analyzed in order to see how well the method returns values of specific parameters of the two species.

As an example, FIG. 13 visualizes a count number distribution measured for a pure TAMRA solution. Values corresponding to the z-axis are logarithm values of the probability to obtain a given pair of count numbers $n_1$ and $n_2$. Fitting of the distribution returns mean number of particles, $cV=1.139\pm0.005$, specific brightness for the "red" channel $q_1=79.4\pm0.5$ kHz, and for the "yellow-green" channel $q_2=50.9\pm0.3$ kHz. In Table 6, results of analysis of test experiments are presented. Samples have not been specified by concentration values calculated from dilution factors of the preparation because adsorption of dye molecules to glass surfaces influences real concentrations significantly. Because of the same reason, concentration values are not well reproduced from sample to sample; a shift of concentration values from realization to realization is also sometimes observable. Specific brightness values are well reproduced, however. Values of statistical errors presented are theoretical values corresponding to the assumption of uncorrelated measurements, multiplied by three, which is an empirical factor. In addition to statistical errors, deviations from sample to sample of a modest size are also noticeable.

TABLE 6

| Sample | Realization number | Mean number of molecules per sample volume, cV | Specific brightness in „red", $q_1$, kHz | Specific brightness in „yellow-green", $q_2$, kHz |
|---|---|---|---|---|
| TAMRA | 1 | 1.128 ± 0.005 | 79.6 ± 0.4 | 51.3 ± 0.3 |
|  | 2 | 1.139 | 79.4 | 50.9 |
|  | 3 | 1.160 | 79.4 | 50.8 |
|  | 4 | 1.171 | 79.0 | 50.6 |
| RRX | 1 | 1.892 ± 0.009 | 48.0 ± 0.3 | 15.63 ± 0.09 |
|  | 2 | 1.859 | 48.0 | 15.63 |
|  | 3 | 1.850 | 47.3 | 15.44 |
|  | 4 | 1.811 | 47.9 | 15.58 |
| TAMRA and RRX | 1 | 0.99 ± 0.05 | 78.0 ± 1.0 | 51.8 ± 1.1 |
|  |  | 1.14 ± 0.05 | 49.1 ± 1.1 | 15.0 ± 0.9 |
|  | 2 | 1.01 | 76.8 | 51.1 |
|  |  | 1.08 | 49.5 | 15.1 |
|  | 3 | 0.99 | 77.9 | 51.8 |
|  |  | 1.03 | 49.3 | 15.1 |
|  | 4 | 0.97 | 76.9 | 51.7 |
|  |  | 1.03 | 50.0 | 15.5 |
| TAMRA and RRX, new sample | 1 | 0.93 ± 0.07 | 74.6 ± 1.3 | 49.6 ± 1.5 |
|  |  | 2.51 ± 0.07 | 47.6 ± 0.8 | 14.7 ± 0.5 |
|  | 2 | 0.98 | 75.2 | 49.2 |
|  |  | 2.38 | 46.8 | 14.2 |
|  | 3 | 0.96 | 75.0 | 49.4 |
|  |  | 2.25 | 48.0 | 14.7 |
|  | 4 | 0.94 | 76.1 | 49.9 |
|  |  | 2.16 | 47.6 | 14.8 |

It is worth noting that distributions measured with mixture are qualitatively different from those measured for pure dyes. FIG. 14 visualizes weighted residuals of fitting a distribution measured with a mixture of TAMRA and RRX. The upper graph corresponds to the adequate analysis when two species were assumed to be present; residuals are scattered quite randomly and uniformly. The lower graph corresponds to the assumption that only a single species is present; there is a significant difference between the measured and the calculated distribution in this case, $n_1$ is the count number obtained by the "red" detector, and $n_2$ is the count number obtained by the "yellow-green" detector.

In traditional fluorescence polarization studies, average intensities of two polarization components of fluorescence are measured. Fluctuations of the intensities are not of direct interest there but are considered rather as a source of statistical errors. Changes in the fluorescence polarization values of a sample containing a fluorescently labeled binding partner reflect changes in molecular volume and, hence, provide direct information on equilibrium binding. Fluorescence polarization measurements can also be performed in real-time, allowing the kinetic analysis of association and dissociation reactions. One of the most widely-used fluorescence polarization applications is the competitive immunoassay used for the detection of therapeutic and illicit drugs. The method of fluorescence polarization has been used for clinical immunoassays for more than a decade. The homogeneous FPIA (fluorescence polarization in immunoassays) has well-accepted advantages over conventional heterogeneous immunoassays like RIA or ELISA. However, it fails if multi-binding step reactions are to be investigated because the separation of individually polarized species is impossible. Therefore, ligand binding curves only demonstrate the overall decrease of polarization, meaning the mechanistic binding constants cannot be determined. Further limitations are seen in sample volume as well as in mass restrictions.

With a two-dimensional fluorescence intensity distribution analysis according to the present invention, the full content of information usually buried in fluorescence anisotropy can be utilized, thereby overcoming the limitations mentioned above. 2D-FIDA directly determines two specific quantities per each fluorescence species in one measurement; the fluorescence intensity per molecule and the anisotropy of a given model. Based on this supplementary information, the delineation of all participating species and even the quantification of the binding behavior is possible. 2D-FIDA anisotropy is an ideal tool for the quantitative description of systems exhibiting multiple binding step, aggregation and multimerization phenomena.

Theophylline therapy has been a cornerstone of asthma therapy for several years and, therefore, there is a strong demand for assaying and fine-tuning the theophylline level in serum. To demonstrate the capabilities of the present invention, the binding of theophylline antigens to anti-theophylline antibodies from a polyclonal anti-theophylline serum has been investigated. The antigens were labeled with 5'-carboxytetramethylrhodamine (TAMRA) with and without an incorporated spacer. In classical FP analysis these conjugates exhibited low anisotropy values (0.037 and 0.055 respectively) upon interacting with the antibody. Therefore they form a critical basis for illustrating the sensitivity of the present invention.

For the binding experiments the stock solutions of antibody and antigens were diluted in a PBS buffer with 0.05% Tween 20. After mixing the compounds, the mixture was incubated for 30 minutes at room temperature. Matching the spectral properties of the conjugates the system was excited at the 543 nm line of a He/Ne laser (Uniphase). As two examples, measured joint distributions of photon count numbers and results of 2D-FIDA applied to samples at different antibody dilution values but a constant ligand concentration of [L]=2 nM are illustrated by FIGS. 15 and 16. Antibody concentrations are in arbitrary units referring to effective dilutions. Water background was below 1 kHz in each detection channel.

In the two-color fluorescence intensity distribution analysis according to the present invention, two detectors are spectrally tuned to monitor fluorescence from two labels of different color. In the assay type described below, ligand molecules are labeled in "green". Since each vesicle carries a high number of receptors, vesicles in samples with a low binding degree can be distinguished from vesicles in samples with high binding degree by a significantly higher specific brightness in "green". Vesicles are additionally stained in "red". Specific brightness of vesicles in "red" is not altered by binding of ligand molecules, but straining in "red" is a means to increase contrast between free ligand molecules (which are nearly invisible in "red") and vesicles (which in the case of extremely low binding may be of nearly the same brightness in "green" as free ligand molecules). Contributions from the two fluorescent species of a single sample to the measured 2-dimensional distribution of the numbers of photon counts are very different in this assay type indeed and therefore the analysis is highly reliable.

To demonstrate the advantages of a two-dimensional fluorescence intensity, distribution analysis according to the present invention, the binding of TAMRA-labeled somatostatin-14 (SMS14-5TAMRA) to, the hum type-2 high affinity somatostatin receptor SSTR-2 (P. Schoeffter, et al., Eur. J. Pharm., 289, 163–173, 1995) has been chosen as biological system. The receptor was expressed by CCL39bsst2 cells. Vesicles were prepared from this cell line and stained by the lipophilic tracer $DiC_{10}(5)$. The binding reaction was carried out in 10 mM HEPES (pH 7.6), 5 mM $MgCl_2$, 0.01% (w/v) fluorosurfactant FC-135, 133% DMSO in the presence of protease inhibitors. A schematical drawing of the principle of the assay is shown in FIGS. 17.

For excitation of fluorescence of the two spectrally distinct labels, the 532 nm line of a Neodym:Yag laser attenuated to 250 μW and the 632 nm line of a He-Ne laser attenuated to 25 μW were simultaneously used. In order to minimize misalignment of the two laser beams, they both passed through a single optical fiber before being focussed by the microscope. Also, the collected fluorescence beam passed a single pinhole before being splitted for the two detectors. An optical band-pass filter with the center wavelength 590 nm, FWHM 60 nm, and another one with the center wavelength 690 nm, FWHM 40 nm were used in front of the two detectors, monitoring fluorescence from the two labels separately. Because vesicles are slowly diffusing particles, in this experiment an area of 0.05 $mm^2$ of each sample was scanned, using sinusoidal beam scanning of 25 Hz frequency, 100 μm amplitude in one direction, and sample scanning of 500 μm per 8 s data collection time in the other direction.

Figure 18A:
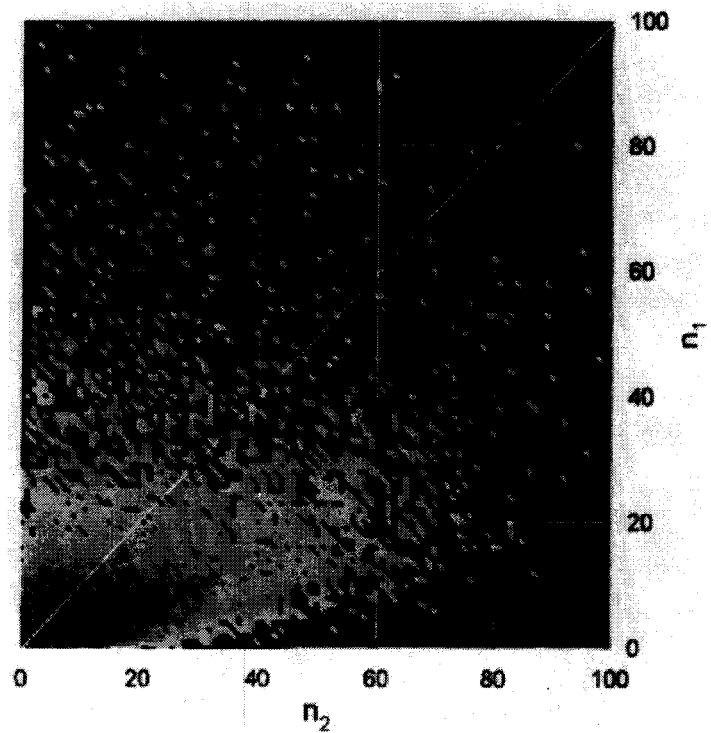
Figure 18B:
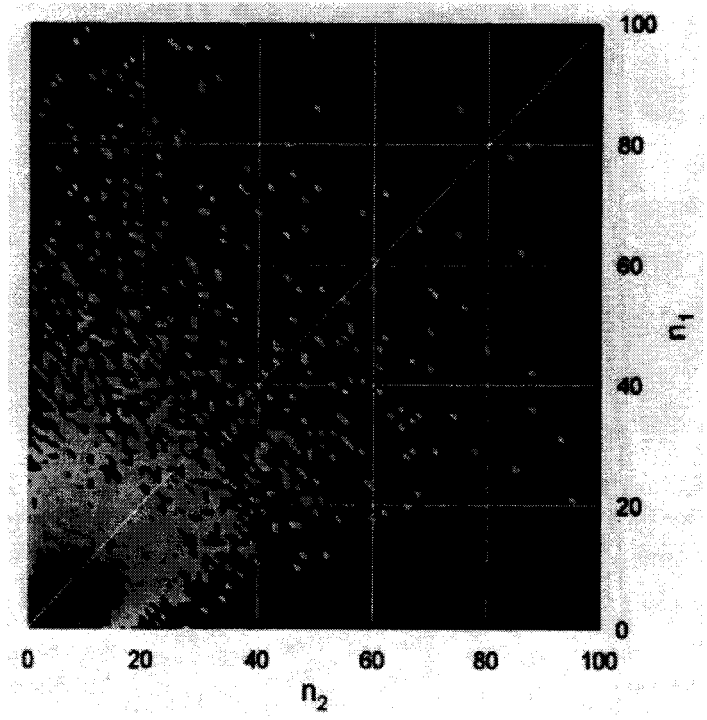

In FIG. 18 two typical examples of count number distributions corresponding to a high and a low degree of binding are compared. In FIG. 18B, the vesicle bound ligand (SMS14-5AMRA) was competed off by the addition of a large excess of non fluorescent competitor (SRIF-14, SIGMA; 1 μm competitor, 3 nM total ligand). It is clearly visible that the distribution obtained in the absence of competitor (FIG. 18A) is more expanded in the $n_2$ direction than in the presence of competitor. The $n_2$ direction represents the green fluoresce of the labeled ligand and, hence, is a measure for the ligand binding.

2D-FIDA according to the present invention was applied to each of the measured distributions. Using a two-component fit algorithm, both the concentration (particle number in the confocal volume) and the fluorescence brightness values for the free ligand and the ligand bound to vesicles were obtained. The vesicles are well separated from the free ligand even in the presence of competitor (low binding). Addition of competitor leads to a decrease in the green fluorescence of the vesicles and an increase in the concentration of free ligand. The fact that the ligand does not completely disassociate from the vesicles is due to unspecific binding which is dependent on the amount of vesicles used in the assay.

Next, the competitor has been titrated from 1 μM down to 10 pM (10 measurements each) in order to record a dose-response curve and to determine the $EC_{50}$ value. As shown in FIG. 19, 2D-FIDA analysis leads to a typical sigmoidal competition curve with very low standard deviations. The calculated $EC_{50}$ value is 0.87 nM which is in good agreement said $EC_{50}$ values obtained using other evaluation methods (data not shown). Thus, it is not only possible to differentiate between high and low binding but also small changes in the binding degree can be resolved with 2D-FIDA analysis according to the present invention. This is in particular important if one aims at the identification of assay inhibitors ("hits") in high throughput screening. In summary, 2D-FIDA analysis is a well-suited and highly reliable method for vesicle-based binding assays and has already been successfully applied in high throughput screening.

Reference is now made to FIG. 20. According to a preferred embodiment, numbers of photon counts $\{n_j\}$ subject to determination of a distribution function $\hat{P}(n)$ in step b) are derived from numbers of photon counts in primary time intervals $\{N_j\}$ by addition of numbers of photon counts from primary time intervals according to a predetermined rule. Out might e.g. be interested in choosing numbers of photon counts $\{n_j\}$ subject to determination of a distribution function $\hat{P}(n)$ which are calculated from the numbers of photon counts in primary time intervals $\{N_j\}$ according to the rule $$n_i = \sum_{k=1}^{M} N_{Mi+k},$$

where M is in integer number expressing how many times the time interval in which $\{n_j\}$ is determined is longer than the primary time interval. Line N shows the primary time interval windows. Line $n_j$ indicates the primary time windows chosen to calculate $n_j$ according to the rule.

FIG. 21 shows a further embodiment in which numbers of photon counts ($n_i$) are derived from predetermined primary tine intervals according to a rule in which primary time intervals are separated by a time delay. In particular, the, following rule can be applied:

$$n_i = \sum_{k=1}^{M} (N_{Mi+k} + N_{M(i+L)+k}),$$

where M and L are positive integer numbers, $\{n_i\}$ are numbers of photon counts subject to determination of a distribution function $\hat{P}(n)$, and $\{N_j\}$ are the numbers of photon counts in primary time intervals.

What is claimed is:

1. A method for characterizing fluorescent molecules or other particles in samples comprising the steps of
   a) monitoring fluctuating intensity of fluorescence emitted by the molecules or other particles in at least one measurement volume of a non-uniform spatial brightness profile by measuring numbers of photon counts in primary time intervals by a single or more photon detectors, b) determining at least one distribution function of numbers of photon counts, $\hat{P}(n)$, from the measured numbers of photon counts, c) determining physical quantities characteristic to said particles by fitting the experimentally determined distribution function of numbers of photon counts, wherein the fitting procedure involves calculation of a theoretical distribution function of the number of photon counts P(n) through its generating function, defined as $$G(\bar{\zeta}) = \sum_n \bar{\zeta}^n P(n).$$

2. A method according to claim 1 wherein the primary time intervals are consecutive intervals of equal width.

3. A method according to claim 1 wherein in step b) numbers of photon counts $\{n_i\}$ subject to determination of a distribution function $\hat{P}(n)$ are derived from numbers of photon counts in primary time intervals $\{N_j\}$ by addition of numbers of photon counts from primary time intervals according to a predetermined rule.

4. A method according to claim 3 wherein in step b) numbers of photon counts $\{n_i\}$ subject to determination of a distribution function $\hat{P}(n)$ are calculated from the numbers of photon counts in primary time intervals $\{N_j\}$ according to the rule $$n_i = \sum_{k=1}^{M} N_{Mi+k},$$

where M is an integer number expressing how many times the time interval in which $\{n_i\}$ is determined is longer than the primary time interval.

5. A method according to claim 3 wherein in step b) numbers of photon counts $\{n_i\}$ are calculated from predetermined primary time intervals according to a rule in which primary time intervals are separated by a time delay.

6. A method according to claim 5 wherein in step b) numbers of photon counts $\{n_i\}$ subject to determination of a distribution function $\hat{P}(n)$ are calculated from the numbers of photon counts in primary time intervals $\{N_j\}$ according to the rule $$n_i = \sum_{k=1}^{M} (N_{Mi+k} + N_{M(i+L)+k}),$$

where M and L are positive integer numbers.

7. A method according to claim 6 wherein in step c) a set of distribution functions with different values of M and/or L are fitted jointly.

8. A method according to claim 1 wherein in step b) a set of distribution functions $\hat{P}(n)$ is determined according to a set of different rules, said set of distribution functions being fitted jointly in stop c).

9. A method according to claim 1 wherein at least one of the physical quantities of step c) is concentration of particles.

10. A method according to claim 1 wherein at least one of the physical quantities of step c) is specific brightness of particles.

11. A method according to claim 1 wherein at least one of the physical quantities of step c) is diffusion coefficient.

12. A method according to claim 1 wherein the generating function is calculated using the expression $$G(\xi) = \exp[\int dq c(q) \int d^3 r (e^{(\xi-1)qTB(r)} - 1)],$$

where c(q) is the density of particles with specific brightness q, T is the length of the counting interval and B(r) is the spatial brightness profile as a function of coordinates.

13. A method according to claim 1 wherein the argument of the generating function is selected in the form $\xi = e^{-ip}$ and a fast Fourier transform algorithm is used in calculation of the theoretical distribution of the number of photon counts out of its generating function.

14. A method according to claim 1 wherein in step c) when calculating the theoretical distribution P(n), the spatial brightness profile is modelled by a mathematical relationship between volume and spatial brightness.

15. A method according to claim 14 wherein in step c) who calculating the theoretical distribution P(n), the spatial brightness profile is modelled by the following expression:

$$\frac{dV}{dx} = a_1 x + a_2 x^2 + a_3 x^3,$$

where dV denotes a volume element, x denotes logarithm of the relative spatial brightness, and $a_1$, $a_2$ and $a_3$ empirically estimated parameters.

16. A method according to claim 1 wherein in step a) a confocal microscope is used for monitoring the intensity of fluorescence.

17. Use of a confocal apparatus for performing the method according to claim 1 comprising:

a radiation are (12) for providing excitation radiation (14), an objective (22) for focusing the excitation radiation (14) into a measurement volume (26), a detector (42) for detecting emission radiation (30) that stems from the measurement volume (26), and an opaque means (44) positioned in the pathway (32) of the emission radiation (30) or excitation radiation (14) for erasing the central part of the emission radiation (30) or excitation radiation (14).

* * * * *

UNITED STATES PATENT AND TRADEMARK OFFICE
CERTIFICATE OF CORRECTION

PATENT NO. : 6,376,843 B1
DATED : April 23, 2002
INVENTOR(S) : Kaupo Palo

It is certified that error appears in the above-identified patent and that said Letters Patent is hereby corrected as shown below:

Title page,
Item [57], ABSTRACT,

Line 8, change " $\hat{P}(n)$ " to -- $\hat{P}(\mathbf{n})$ --.

Line 13, change "P(n)" to -- $P(\mathbf{n})$ --.

Column 1,
Line 47, change "P(n)" to -- $P(\mathbf{n})$ --.

Column 3,
Lines 7 and 16, change "$P_i(n)$" to -- $P_i(\mathbf{n})$ --.

Line 59, change " $\hat{P}(n)$ " to -- $\hat{P}(\mathbf{n})$ --.

Column 4,
Lines 28, 33, 45 and 55, change "$\{n_i\}$" to -- $\{\mathbf{n}_i\}$ --.

Lines 29, 34, 57 and 61, change " $\hat{P}(n)$ " to -- $\hat{P}(\mathbf{n})$ --.

Column 5,
Line 38, change "P(n)" to -- $P(\mathbf{n})$ --.

Column 6,
Line 43, change "P(n)" to -- $P(\mathbf{n})$ --.

Column 10,
Line 57, change "$P(n_1,n_2)$" to -- $P(\mathbf{n}_1,\mathbf{n}_2)$ --.

Column 11,
Line 16, change "$P(n_1,n_2)$" to -- $P(\mathbf{n}_1,\mathbf{n}_2)$ --.

Column 12,
Line 20, change "$P(n_1,n_2)$" to -- $P(\mathbf{n}_1,\mathbf{n}_2)$ --.

Column 15,
Lines 59 and 65, change "$\{n_i\}$" to -- $\{\mathbf{n}_i\}$ --.

Line 60, change " $\hat{P}(n)$ " to -- $\hat{P}(\mathbf{n})$ --.

UNITED STATES PATENT AND TRADEMARK OFFICE
CERTIFICATE OF CORRECTION

PATENT NO. : 6,376,843 B1
DATED : April 23, 2002
INVENTOR(S) : Kaupo Palo

It is certified that error appears in the above-identified patent and that said Letters Patent is hereby corrected as shown below:

Column 16,
Line 19, change " $\hat{P}(n)$ " to -- $\hat{P}(\mathbf{n})$ --.

Column 17,
Line 3, change "n" to -- $\mathbf{n}$ --.

Column 18,
Line 41, change "P(n)" to -- $P(\mathbf{n})$ --.

Column 19,

Line 11, change " $\hat{P}(n)$ " to -- $\hat{P}(\mathbf{n})$ --.

Column 26,
Line 30, change "$\{n_j\}$" to -- $\{\mathbf{n}_j\}$ --.

Lines 31 and 57, change " $\hat{P}(n)$ " to -- $\hat{P}(\mathbf{n})$ --.

Line 46, change "$\{n_i\}$" to -- $\{\mathbf{n}_i\}$ --.

Column 27,
Lines 2, 26, 43 and 55, change " $\hat{P}(n)$ " to -- $\hat{P}(\mathbf{n})$ --.

Lines 24, 37, and 41, change "$\{n_i\}$" to -- $\{\mathbf{n}_i\}$ --.

Signed and Sealed this

Twenty-seventh Day of December, 2005

JON W. DUDAS
*Director of the United States Patent and Trademark Office*